(12) United States Patent
Rudakov

(10) Patent No.: US 10,813,644 B2
(45) Date of Patent: Oct. 27, 2020

(54) OCCLUSIVE IMPLANT AND DELIVERY SYSTEM

(71) Applicant: ArtVentive Medical Group, Inc., San Marcos, CA (US)

(72) Inventor: Leon Rudakov, San Marcos, CA (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 18 days.

(21) Appl. No.: 15/476,873

(22) Filed: Mar. 31, 2017

(65) Prior Publication Data
US 2017/0319214 A1 Nov. 9, 2017

Related U.S. Application Data

(60) Provisional application No. 62/317,361, filed on Apr. 1, 2016.

(51) Int. Cl.
*A61B 17/12* (2006.01)
*A61B 17/00* (2006.01)

(52) U.S. Cl.
CPC .... *A61B 17/12109* (2013.01); *A61B 17/1204* (2013.01); *A61B 17/1215* (2013.01); *A61B 17/12036* (2013.01); *A61B 17/12163* (2013.01); *A61B 17/12172* (2013.01); *A61B 17/12177* (2013.01); *A61B 2017/00867* (2013.01); *A61B 2017/00884* (2013.01); *A61B 2017/1205* (2013.01); *A61B 2017/12054* (2013.01)

(58) Field of Classification Search
CPC ................................. A61B 2017/12054; A61B 2017/12063–12072; A61B 2017/12086; A61B 2017/1205–12095
See application file for complete search history.

(56) References Cited

U.S. PATENT DOCUMENTS

| 3,805,767 A | 4/1974 | Erb |
| 3,868,956 A | 3/1975 | Alfidi et al. |
| 3,877,434 A | 4/1975 | Ferguson et al. |

(Continued)

FOREIGN PATENT DOCUMENTS

| DE | 202008007775 U1 | 8/2008 |
| EP | 1166721 A2 | 1/2002 |

(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.

(Continued)

*Primary Examiner* — Katrina M Stransky
*Assistant Examiner* — Brigid K Byrd
(74) *Attorney, Agent, or Firm* — Nathan S. Smith; Sujohn Das; Morgan, Lewis & Bockius LLP

(57) ABSTRACT

An occlusive implant can be delivered into a body vessel using a delivery assembly that can engage with at least a portion of the implant. The assembly can utilize an engagement member and an engagement socket or a catheter or sheath to removably couple the engagement member with the implant. When the implant is advanced to a target location in the body vessel, the implant can be released to restrict flow of a fluid through the vessel and/or promote occlusion of the vessel.

19 Claims, 25 Drawing Sheets

(56) References Cited

U.S. PATENT DOCUMENTS

| | | |
|---|---|---|
| 3,918,431 A | 11/1975 | Sinnreich |
| 4,013,063 A | 3/1977 | Bucalo |
| 4,245,623 A | 1/1981 | Erb |
| 4,503,569 A | 3/1985 | Dotter |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,878,906 A | 11/1989 | Lindemann et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,357 A * | 9/1992 | Rose .............. A61B 17/29 606/49 |
| 5,147,370 A | 9/1992 | McNamara et al. |
| 5,177,075 A | 1/1993 | Suto et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A | 12/1995 | Limon |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,601,818 A | 2/1997 | Freeman et al. |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,702,419 A | 12/1997 | Berry et al. |
| 5,725,552 A | 3/1998 | Kotula et al. |
| 5,733,329 A | 3/1998 | Wallace et al. |
| 5,772,668 A | 6/1998 | Summers et al. |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,868,782 A | 2/1999 | Frantzen |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,957,929 A | 9/1999 | Brenneman |
| 5,976,179 A | 11/1999 | Inoue |
| 5,979,446 A | 11/1999 | Loy |
| 5,989,242 A * | 11/1999 | Saadat ............ A61B 17/12022 606/1 |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,083,257 A | 7/2000 | Taylor et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,258,119 B1 | 7/2001 | Hussein et al. |
| 6,277,103 B1 | 8/2001 | Lauer |
| 6,283,983 B1 | 9/2001 | Makower et al. |
| 6,296,622 B1 * | 10/2001 | Kurz ............... A61B 17/12022 604/93.01 |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,485,524 B2 | 11/2002 | Strecker |
| 6,488,700 B2 | 12/2002 | Klumb et al. |
| 6,506,204 B2 | 1/2003 | Mazzocchi |
| 6,514,285 B1 | 2/2003 | Pinchasik |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,572,648 B1 | 6/2003 | Klumb et al. |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,790,223 B2 | 9/2004 | Reever |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |
| 7,001,409 B2 | 2/2006 | Amplatz |
| 7,011,643 B2 | 3/2006 | Villafana et al. |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |

(56) References Cited

U.S. PATENT DOCUMENTS

| | | |
|---|---|---|
| 7,398,780 B2 | 7/2008 | Callister et al. |
| 7,434,578 B2 | 10/2008 | Dillard et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,862,602 B2 | 1/2011 | Licata et al. |
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,298,257 B2 | 10/2012 | Sepetka et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 8,808,342 B2 | 8/2014 | Ludwig |
| 8,834,544 B2 | 9/2014 | Gerrans et al. |
| 9,247,942 B2 | 2/2016 | Rudakov et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0173839 A1 | 11/2002 | Leopold et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0130684 A1 | 7/2003 | Brady et al. |
| 2003/0153972 A1 | 8/2003 | Helmus |
| 2003/0158515 A1 | 8/2003 | Gonzalez et al. |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0212452 A1 | 11/2003 | Zadno-Azizi et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0023415 A1 | 2/2004 | Sokolov et al. |
| 2004/0029994 A1 | 2/2004 | Cheng et al. |
| 2004/0034363 A1* | 2/2004 | Wilson ............ A61B 17/12022 606/108 |
| 2004/0044360 A1 | 3/2004 | Lowe |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0049608 A1 | 3/2005 | Aznoian et al. |
| 2005/0051163 A1 | 3/2005 | Deem et al. |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1 | 3/2006 | Mirizzi et al. |
| 2006/0111771 A1 | 5/2006 | Ton et al. |
| 2006/0111801 A1 | 5/2006 | Weare et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0195175 A1 | 8/2006 | Bregulla |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0166852 A1* | 7/2007 | Brown ............ A61B 17/0057 438/26 |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0046092 A1 | 2/2008 | Davis et al. |
| 2008/0086214 A1 | 4/2008 | Hardin et al. |
| 2008/0103522 A1 | 5/2008 | Steingisser et al. |

(56) References Cited

U.S. PATENT DOCUMENTS

| | | |
|---|---|---|
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0221657 A1 | 9/2008 | Laroya et al. |
| 2008/0221666 A1 | 9/2008 | Licata et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0024072 A1 | 1/2009 | Criado et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0094395 A1 | 4/2010 | Kellett |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0092997 A1 | 4/2011 | Kang |
| 2011/0124958 A1 | 5/2011 | Nelson |
| 2011/0125132 A1 | 5/2011 | Krolik et al. |
| 2011/0172697 A1 | 7/2011 | Jonsson |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089102 A1 | 4/2012 | Chomas et al. |
| 2012/0089216 A1 | 4/2012 | Rapaport et al. |
| 2012/0095489 A1 | 4/2012 | Rudakov et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245614 A1 | 9/2012 | Drasler |
| 2012/0245620 A1 | 9/2012 | Gilson et al. |
| 2012/0245668 A1 | 9/2012 | Kariniemi et al. |
| 2012/0253120 A1 | 10/2012 | Callister et al. |
| 2012/0259354 A1 | 10/2012 | Kellett |
| 2012/0277842 A1 | 11/2012 | Kunis |
| 2012/0283768 A1 | 11/2012 | Cox et al. |
| 2012/0289988 A1 | 11/2012 | Riina et al. |
| 2012/0289994 A1 | 11/2012 | Larson et al. |
| 2012/0296408 A1 | 11/2012 | Jones et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053758 A1 | 2/2013 | Kibbe |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0058435 A1* | 2/2014 | Jones ............... A61B 17/1214 606/200 |
| 2014/0073903 A1 | 3/2014 | Weber et al. |
| 2014/0128780 A1 | 5/2014 | Kennedy et al. |
| 2014/0207180 A1 | 7/2014 | Ferrera |
| 2014/0215792 A1 | 8/2014 | Leopold et al. |
| 2014/0222059 A1 | 8/2014 | Leopold et al. |
| 2014/0257369 A1 | 9/2014 | Leopold et al. |
| 2014/0277085 A1 | 9/2014 | Mirigian et al. |
| 2014/0371716 A1 | 12/2014 | Rudakov |
| 2014/0371777 A1 | 12/2014 | Rudakov et al. |
| 2014/0371778 A1 | 12/2014 | Rudakov et al. |
| 2015/0057700 A1 | 2/2015 | Chen et al. |
| 2015/0157329 A1 | 6/2015 | Rudakov et al. |
| 2015/0157333 A1 | 6/2015 | Leopold et al. |
| 2015/0223821 A1 | 8/2015 | Rudakov et al. |
| 2015/0290437 A1 | 10/2015 | Rudakov et al. |
| 2015/0313602 A1 | 11/2015 | Rudakov |
| 2015/0342611 A1 | 12/2015 | Leopold et al. |
| 2016/0022272 A1 | 1/2016 | Rudakov et al. |
| 2016/0101271 A1 | 4/2016 | Rudakov et al. |
| 2017/0095258 A1* | 4/2017 | Tassoni ............ A61B 17/12145 |

FOREIGN PATENT DOCUMENTS

| | | |
|---|---|---|
| EP | 1188413 | 3/2002 |
| EP | 1317908 A2 | 6/2003 |
| EP | 1600110 A1 | 11/2005 |
| EP | 1707233 A2 | 10/2006 |
| EP | 1752112 A1 | 2/2007 |
| EP | 1813196 A1 | 8/2007 |
| EP | 1820436 A2 | 8/2007 |
| EP | 1852073 A1 | 11/2007 |
| EP | 2248471 A1 | 11/2010 |
| EP | 2366362 A1 | 9/2011 |
| EP | 2366363 A1 | 9/2011 |
| EP | 2366364 A1 | 9/2011 |
| EP | 2404580 A1 | 1/2012 |

(56) References Cited

FOREIGN PATENT DOCUMENTS

| | | |
|---|---|---|
| EP | 2583636 A1 | 4/2013 |
| GB | 2404860 A | 2/2005 |
| GB | 2494820 A | 3/2013 |
| JP | H 07-000405 | 1/1995 |
| JP | H 07-185011 A | 7/1995 |
| JP | 2006-181015 A | 7/2006 |
| JP | 2010-532180 A | 10/2010 |
| JP | 2012-525859 A | 10/2012 |
| WO | WO-83/00997 A1 | 3/1983 |
| WO | WO-92/14408 A1 | 9/1992 |
| WO | WO-94/000179 A1 | 1/1994 |
| WO | WO-95/24158 A1 | 9/1995 |
| WO | WO-95/25480 A1 | 9/1995 |
| WO | WO-95/32018 A1 | 11/1995 |
| WO | WO-96/18361 A1 | 6/1996 |
| WO | WO-97/13463 A1 | 4/1997 |
| WO | WO-97/13471 A1 | 4/1997 |
| WO | WO-97/27893 A1 | 8/1997 |
| WO | WO-97/27897 A1 | 8/1997 |
| WO | WO-97/27898 A1 | 8/1997 |
| WO | WO-97/31672 A1 | 9/1997 |
| WO | WO-98/08456 A1 | 3/1998 |
| WO | WO-98/31308 A1 | 7/1998 |
| WO | WO-98/34546 A1 | 8/1998 |
| WO | WO-98/46115 A2 | 10/1998 |
| WO | WO-98/46119 A1 | 10/1998 |
| WO | WO-99/12484 A1 | 3/1999 |
| WO | WO-99/23976 A1 | 5/1999 |
| WO | WO-99/25273 A1 | 5/1999 |
| WO | WO-99/44542 A2 | 9/1999 |
| WO | WO-99/48545 A1 | 9/1999 |
| WO | WO-99/49793 A1 | 10/1999 |
| WO | WO-99/49910 A2 | 10/1999 |
| WO | WO-99/62430 A1 | 12/1999 |
| WO | WO-00/09195 A1 | 2/2000 |
| WO | WO-00/16847 A1 | 3/2000 |
| WO | WO-00/27303 A2 | 5/2000 |
| WO | WO-00/67671 A1 | 11/2000 |
| WO | WO-01/032254 A1 | 5/2001 |
| WO | WO-01/64112 A1 | 9/2001 |
| WO | WO-01/080776 A1 | 11/2001 |
| WO | WO-01/080777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 A1 | 9/2003 |
| WO | WO-03/073962 A1 | 9/2003 |
| WO | WO-03/101518 A1 | 12/2003 |
| WO | WO-2004/006804 A1 | 1/2004 |
| WO | WO-2004/073557 A2 | 9/2004 |
| WO | WO-2005/020786 A2 | 3/2005 |
| WO | WO-2005/092241 A1 | 10/2005 |
| WO | WO-2005/117755 A2 | 12/2005 |
| WO | WO-2006/017470 A2 | 2/2006 |
| WO | WO-2006/028943 A1 | 3/2006 |
| WO | WO-2006/031602 A1 | 3/2006 |
| WO | WO-2006/034153 A2 | 3/2006 |
| WO | WO-2006/039216 A2 | 4/2006 |
| WO | WO-2006/074163 A2 | 7/2006 |
| WO | WO-2006/096342 A1 | 9/2006 |
| WO | WO-2006/134354 A1 | 12/2006 |
| WO | WO-2007/061927 A2 | 5/2007 |
| WO | WO-2007/070544 A2 | 6/2007 |
| WO | WO-2007/085373 A1 | 8/2007 |
| WO | WO-2007/127351 A1 | 11/2007 |
| WO | WO-2007/149844 A2 | 12/2007 |
| WO | WO-2008/010197 A2 | 1/2008 |
| WO | WO-2008/022327 A2 | 2/2008 |
| WO | WO-2008/100790 A2 | 8/2008 |
| WO | WO-2008/112501 A2 | 9/2008 |
| WO | WO-2008/153653 A1 | 12/2008 |
| WO | WO-2009/061419 A1 | 5/2009 |
| WO | WO-2009/064618 A1 | 5/2009 |
| WO | WO-2009/077845 A2 | 6/2009 |
| WO | WO-2009/088905 A1 | 7/2009 |
| WO | WO-2009/124288 A1 | 10/2009 |
| WO | WO-2009/126747 A1 | 10/2009 |
| WO | WO-2010/009019 A1 | 1/2010 |
| WO | WO-2010/047644 A1 | 4/2010 |
| WO | WO-2010/075565 A2 | 7/2010 |
| WO | WO-2010/085344 A1 | 7/2010 |
| WO | WO-2010/096717 A1 | 8/2010 |
| WO | WO-2010/130617 A1 | 11/2010 |
| WO | WO-2010/135352 A1 | 11/2010 |
| WO | WO-2010/146581 A1 | 12/2010 |
| WO | WO-2010/148246 A2 | 12/2010 |
| WO | WO-2011/011581 A2 | 1/2011 |
| WO | WO-2011/153304 A1 | 12/2011 |
| WO | WO-2011/159913 A2 | 12/2011 |
| WO | WO-2011/163157 A2 | 12/2011 |
| WO | WO-2012/002944 A1 | 1/2012 |
| WO | WO-2012/040380 A1 | 3/2012 |
| WO | WO-2012/054065 A1 | 4/2012 |
| WO | WO-2012/067724 A1 | 5/2012 |
| WO | WO-2012/109367 A1 | 8/2012 |
| WO | WO-2012/111137 A1 | 8/2012 |
| WO | WO-2012/120490 A2 | 9/2012 |
| WO | WO-2012/131672 A2 | 10/2012 |
| WO | WO-2012/134761 A1 | 10/2012 |
| WO | WO-2012/135859 A2 | 10/2012 |
| WO | WO-2012/166804 A1 | 12/2012 |
| WO | WO-2013/055703 A1 | 4/2013 |
| WO | WO-2013/059511 A1 | 4/2013 |
| WO | WO-2013/067299 A1 | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.

Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.

DeSouza et al., Embolization with detachable Balloons—Applications outside the head, Clinical Radiology, Apr. 21, 1992, pp. 170-175, vol. 46.

Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.

Hawkins et al., The Permeability of Detachable Latex Rubber Balloons—An In Vitro Study, Investigative Radiology, Dec. 1987, pp. 969-972, vol. 22.

Hirai et al., Emergency Balloon Embolization for Carotid Artery Rupture Secondary to Postoperative Infection, Cardiovasc Intervent Radiol, 1996, pp. 50-52, vol. 19.

Kadir et al., Therapeutic Embolization of the Kidney with Detachable Silicone Balloons, The Journal of Urology, Jan. 1983, pp. 11-13, vol. 129.

Kallmes et al., The Use of Hydrocoil for Parent Artery Occlusion, AJNR Am J Neuroradiol, Sep. 2004, pp. 1409-1410, vol. 25.

Kaufman, et al., Detachable Balloon-modified Reducing Stent to Treat Hepatic Insufficiency after Transjugular Intrahepatic Portosystemic Shunt Creation, J Vasc Interv Radiol., May 2003, pp. 635-638, vol. 14, No. 5.

Luo, Chao-Bao et al., Endovascular Treatment of the Carotid Artery Rupture with Massive Hemorrhage, J. Chin Med Assoc., Mar. 2003.

Makita, et al., Guide-Wire-directed Detachable Balloon: Clinical Application in Treatment of Varicoceles, Radiology, 1992, pp. 575-577, vol. 183.

Marshall et al., Treatment of Traumatic Renal Arteriovenous Fistulas by Detachable Silicone Balloon Embolization, The Journal of Urology, Aug. 1979, pp. 237-239, vol. 122.

Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.

Pollak et al., Clinical Results of Transvenous Systemic Embolotherapy with a Neuroradiologic Detachable Balloon, Radiology, May 1994, pp. 477-482, vol. 191, No. 2.

(56) References Cited

OTHER PUBLICATIONS

Reidy et al., Transcatherer occlusion of coronary to bronchial anastomosis by detachable balloon combined with coronary angioplasty at same procedure, Brit Heart J. 1983, pp. 284-287, vol. 49.
Reidy et al., Transcatheter occlusion of a Blalock-Taussig shunt with a detachable balloon in a child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic arterioportal fistula and its treatment with detachable balloon and transcatheter embolization with coils and microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.
Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

\* cited by examiner

OCCLUSIVE IMPLANT AND DELIVERY SYSTEM

CROSS-REFERENCE TO RELATED APPLICATIONS

This application claims the priority benefit of U.S. Provisional Application No. 62/317,361, filed on Apr. 1, 2016, the entirety of which is incorporated herein by reference. The present application also incorporates by reference the disclosures of U.S. patent application Ser. No. 14/101,171, filed on Dec. 9, 2013 (086538-0046), U.S. Provisional Application No. 61/835,406, filed on Jun. 14, 2013 (086538-0032), U.S. Provisional Application No. 61/835,461, filed on Jun. 14, 2013 (086538-0034), U.S. Provisional Application No. 61/836,061, filed on Jun. 17, 2013 (086538-0038), U.S. Provisional Application No. 61/900,321, filed on Nov. 5, 2013 (086538-0040), U.S. Provisional Application No. 61/904,376, filed on Nov. 14, 2013 (086538-0041), U.S. Provisional Application No. 61/904,379, filed on Nov. 14, 2013 (086538-0043), and U.S. Provisional Application No. 61/939,659, filed on Feb. 13, 2014 (086538-0049), U.S. Patent App. No. 61/987,446, filed on May 1, 2014 (086538-0054), U.S. patent application Ser. No. 14/304,868, filed on Jun. 13, 2014 (086538-0057), and U.S. patent application Ser. No. 14/628,096, filed on Feb. 20, 2015 (086538-0063).

FIELD

The subject technology relates generally to apparatuses and methods for blood vessel occlusion using an occlusive implant that has a minimal delivery profile, thereby allowing the implant to be delivered to small-diameter body lumens.

BACKGROUND

Rapid, well-controlled, and safe methods to limit bleeding in vessels have encouraged the development of endovascular devices and techniques, and their introduction into clinical practice. Early devices used balloons, either non-detachable or later detachable, in order to block vessels, for example, in the treatment of carotid-cavernous fistulas and saccular aneurysms.

Typically made from latex or silicone, balloons are delivered to a desired location in a vessel, then inflated in order to physically occlude the vessel. While other devices have since been developed, balloon occlusion remains in use, and is indicated for use in treating a variety of life-threatening conditions, including for example, giant cerebral and skull base aneurysms, traumatic and non-traumatic vessel injury or rupture, vertebro-vertebral arteriovenous fistulas, and pre-operative tumor resections.

Detachable balloons are also useful clinically in procedures outside of neurological intervention. For example, balloons can be useful in flow reduction procedures such as shunt occlusion in patients with transjugular intrahepatic portosystemic shunts and hepatic insufficiency, intrahepatic arterioportal fistulas, treatment of varicoceles, shunt occlusion in patients with a Blalock-Taussig shunt, obliteration of pulmonary arteriovenous fistulas, arteriovenous malformations or aortopulmonary anastomoses, coronary arteriovenous fistulas, or renal arteriovenous fistulas. Detachable balloons are also used in preoperative devascularization before surgical resection of organs such as the kidney.

Additionally, despite the increase in system and implant options for occluding a body lumen, traditional devices and technology have been limited in their ability to reach small body lumens. Accordingly, the present disclosure provides various delivery systems, engagement mechanisms, and implants that function to provide immediate occlusion of a blood vessel as well as reliable, precise placement and minimal or no migration when the implant is released into the blood vessel.

SUMMARY

Some embodiments provided herein relate to vessel occlusion by delivery of radially expandable implants that can achieve immediate total occlusion of blood flow using one or more occlusive components that are coupled to a frame the implant. As noted above, the present disclosure provides delivery systems, engagement mechanisms, and implants that function to provide immediate occlusion of a blood vessel as well as reliable, precise placement and minimal or no migration when the implant is released into the blood vessel. Some embodiments of delivery systems, engagement mechanisms, implants, implant frames, and implant component configurations, expected delivered and expanded dimensions, and a description of target anatomy of some embodiments are provided herein.

The present disclosure provides various embodiments in which an implant can be delivered to a target area within a body lumen that has a very low diameter and therefore is difficult to reach using previous occlusion or delivery methods. Advantageously, some embodiments use a minimal number of components to effectuate occlusion of the body lumen, thus enabling the implant to be delivered using a low profile delivery catheter.

Accordingly, some embodiments provided herein relate to implantation in small blood vessels, such as from about 1 mm to about 20 mm, from about 2 mm to about 10 mm, or from about 3 mm to about 6 mm. The target delivery profile can be from about 1 Fr to about 20 Fr, and in some embodiments, from about 3 Fr to about 10 Fr. The target delivery profile can be about 8 Fr, about 7 Fr, about 6 Fr, about 5 Fr, about 4 Fr, about 3 Fr, or smaller.

Additionally, expansion of the implant can provide sufficient radial force against the inside wall of a vein. Some embodiments can comprise features or means configured to minimize backflow of blood or minimize venous insufficiency. For example, treatment applications for embodiments of the device can include ilio-femoral venous obstruction and chronic iliac venous outflow obstruction as a result of venous disease.

Some embodiments of the implants provided herein can be manufactured via several methods including shape-setting of drawn wire, chemical etching of a NiTi (nitinol) sheet of material, laser cutting of a tubular member, such as a material sheet or tubing, and/or electrical discharge machining (EDM) of a tubular member, such as a material sheet or tubing. Additionally, other alloys may also be employed in some circumstances, such as tantalum titanium and tantalum platinum titanium.

The implants disclosed herein can comprise flexible and/or shape memory materials such that they may be distorted from an expanded shape to a smaller diameter or straight shape to allow for delivery to a target location by way of a minimally invasive catheter-based approach.

In accordance with some embodiments, the implant can comprise a frame and an implant cover, cover component, or cover material. The frame can be covered with a non-permeable material, sealed at one or both ends to occlude blood flow. The cover component can comprise ePTFE tubing, film, and/or suture for attachment purposes. Additionally, the cover component may be fibrous, mesh-like, or impermeable in density.

The implant frame and/or cover component can comprise a collagen coating or collagen treatment to improve anchoring of the implant in the target vessel. The collagen can be configured to promote cell adhesion to implant materials, thereby facilitating improved support for the implant and vessel structure while acting as an anti-migration feature for the implant.

The implant frame can comprise a straight or constant diameter, a tapering diameter, or sections of variable diameter extending over its length, which can facilitate anchoring within a vessel and optimal deployment function.

Some embodiments of the systems and devices disclosed herein address the unmet need for a device that can provide a fast, precise and reliable way to close a bodily lumen. In some embodiments as used herein, occlusion may refer to partial or complete occlusion that can be temporary or permanent.

Frame configurations, expected delivered and expanded dimensions, and a description of target anatomy of some embodiments are provided. Some embodiments are provided by which the assembly, catheter, and/or implant can be advanced over a guidewire, thus allowing treatment of tortuous, distal, or smaller vessels in the vasculature. Aspects of implants, catheters, and delivery devices that can be utilized in combination with the implants, systems, methods, and features disclosed herein are disclosed in: U.S. patent application Ser. No. 12/826,593, filed on Jun. 29, 2010 (086538-0012); U.S. patent application Ser. No. 13/367,338, filed on Feb. 6, 2012 (086538-0018); U.S. patent application Ser. No. 12/906,993, filed on Oct. 18, 2010 (086538-0014); U.S. patent application Ser. No. 13/828,974, filed on Mar. 14, 2013 (086538-0030); U.S. Patent App. No. 61/835,406, filed on Jun. 14, 2013 (086538-0032); U.S. Patent Application No. 61/836,061, filed on Jun. 17, 2013 (086538-0038); U.S. patent application Ser. No. 14/044,794, filed on Oct. 2, 2013 (086538-0039); U.S. Patent App. No. 61/904,376, filed on Nov. 14, 2013 (086538-0041); U.S. patent application Ser. No. 14/101,171, filed on Dec. 9, 2013 (086538-0046); U.S. patent application Ser. No. 14/304,868, filed on Jun. 13, 2014 (086538-0057); U.S. patent application Ser. No. 14/622,729, filed on Feb. 13, 2015 (086538-0063); U.S. patent application Ser. No. 14/697,547, filed on Apr. 27, 2015 (086538-0067), and U.S. patent Ser. No. 14/973,414, filed Dec. 17, 2015 (086538-0074), the entirety of each of which is incorporated herein by reference.

Some embodiments of the implant can be used for purposes of tumor devascularization, calibrated flow and pressure reduction, reducing traumatic bleeding or hemorrhage, high-flow vascular malformations, vascular or airway volume reduction procedures, treatment of a target lesion, treatment and embolization of incompetent venous systems in low extremities (i.e., legs and lower abdominal area), treatment varicose veins in the leg (i.e., great saphenous vein and spider veins in deeper system), attending to other indications such as arterio-venous malformation (AVM), pelvic varices, and other such issues.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1:
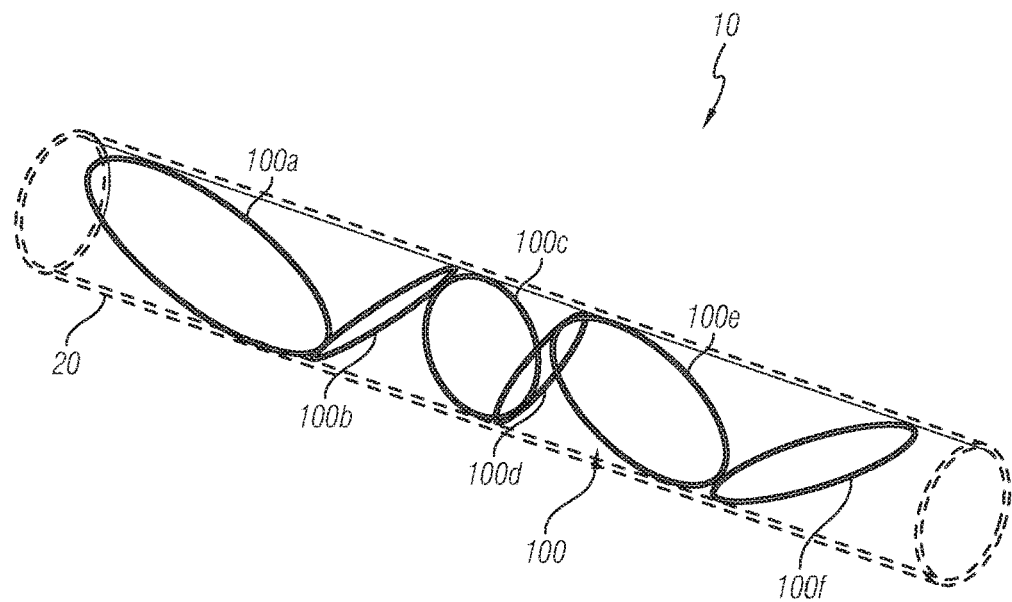
FIG. 1 illustrates a perspective view of an occlusive implant, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

The present disclosure provides various embodiments of implant delivery systems and expandable occlusive implants that have a low-profile delivery configuration through a catheter, as well as methods of using the systems and implants. The implant can at least partially occlude or block flow in a body lumen, such as a blood vessel. Some embodiments can be configured to provide complete and immediate occlusion of target lumen using a low-profile implant having a frame and an occlusive component coupled to the frame. The implant can comprise a frame and a nonstructural occlusive component coupled to the frame that can both be positioned in a substantially linear configuration to minimize the cross-sectional profile of the implant in the delivery configuration. Thus, the implant can provide rapid and/or complete occlusion while enabling the implant, catheter, or system to have a low delivery profile, allowing the implant to be implanted into body lumens having a diameter of between about 1 mm and about 10 mm or between about 1 mm and about 20 mm.

For example, the catheter can define an outer diameter of less than 2 Fr (less than 0.667 mm), about 2 Fr (about 0.667 mm), about 3 Fr (about 1 mm), about 4 Fr (about 1.333 mm), about 5 Fr (about 1.667 mm), about 6 Fr (about 2 mm), about 7 Fr (about 2.333 mm), about 8 Fr (about 2.667 mm), about 9 Fr (about 3 mm), about 10 Fr (about 3.333 mm), about 11 Fr (about 3.667 mm), or about 12 Fr (about 4 mm), about 13 Fr (about 4.333 mm), about 14 Fr (about 5.667 mm), about 15 Fr (about 6 mm), or any dimension therebetween. These dimensions are provided for illustrative purposes only, and the size of the catheter disclosed herein can vary from these sizes.

According to some embodiments, a reduced diameter or reduced cross-sectional profile of the occlusive implant can be achieved by using a frame structure that can be collapsed or elongated into a substantially linear configuration. Further, the frame structure can have a nominal profile that is less than about five or ten times the cross-sectional profile of the filament(s) or wire forming the frame structure. For example, in some embodiments, the frame structure can be formed using at least one elongate wire that is drawn into a substantially linear configuration and moved through a catheter lumen toward the target site. Some embodiments can comprise two or more elongate wires that can be drawn into substantially elongate linear configurations. Accordingly, various embodiments can be provided in which the elongate wires are drawn into a minimum profile configuration that allows the stent to assume a collapsed configuration having a cross-sectional profile that allows the stent to be loaded and delivered using a very small gauge catheter.

Some embodiments of the implant frame can be comprise one or more features, such a variable pitch, an alternating pitch, a consistent pitch, a dual wire loop configuration, a single occlusive member, multiple occlusive members, occlusive members having different structures or material types, occlusive member coatings, and/or other features disclosed herein. Further, some embodiments can be used with valves, covers, fibrous membranes, and the like, such as disclosed in Applicant's copending U.S. patent application Ser. No. 14/304,868, filed on Jun. 13, 2014 (086538-0057), the entirety of which is incorporated herein by reference. Further, in accordance with some embodiments, the implants and delivery systems can be used in combination with image-guided placement techniques, such as fluoroscopy and the like. Additional details regarding these and other features are provided further below.

Occlusive Implants

Figure 2:
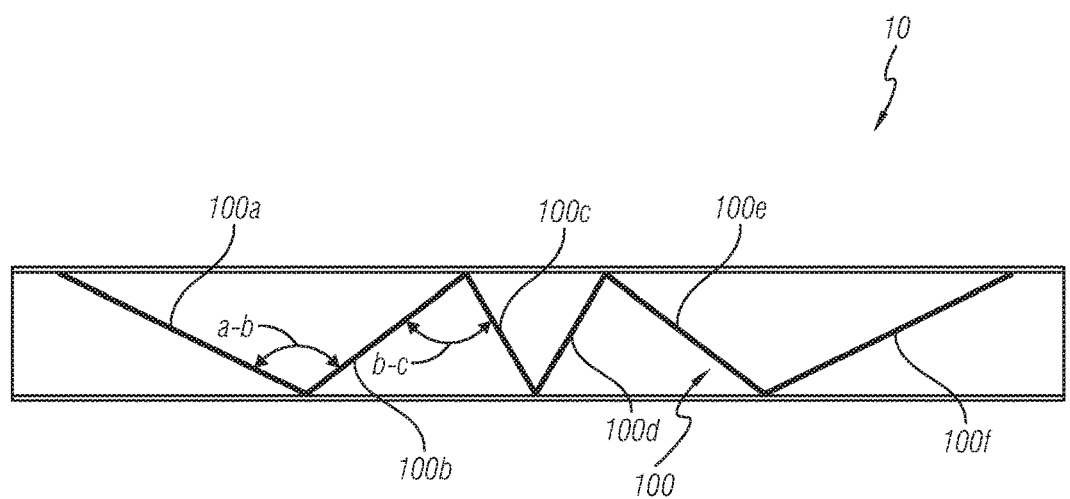
FIG. 2 illustrates a side section view of the occlusive implant of FIG. 1.

FIGS. 1 and 2 illustrate an occlusive implant 10 within a lumen 20. In some embodiments, the occlusive implant 10 can comprise a frame 100 forming a one or more hoop structure. In some embodiments, a plurality of hoop structures (e.g., 100a, 100b, 100c, 100d, 100e, and 100f) are coupled together.

Figure 3:
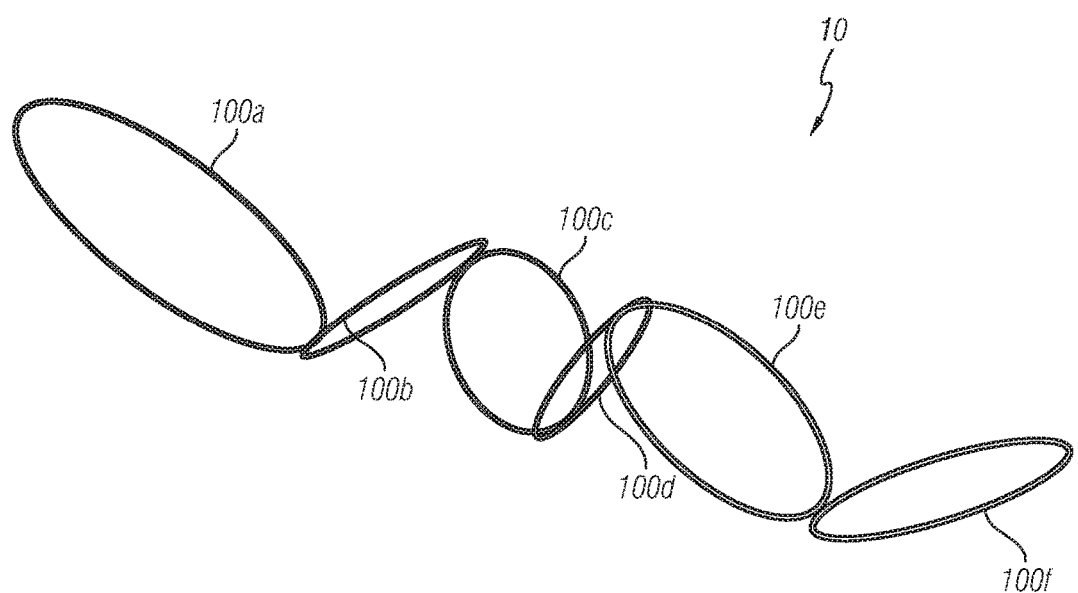
FIG. 3 illustrates a perspective view of an occlusive implant, according to some embodiments.

Referring to the side section view of FIG. 2, when an occlusive implant 10 with a plurality of hoop structures is positioned within a lumen 20, an angle is formed between each pair adjacent coupled hoop structures. For example, referring to FIG. 2 and FIG. 3, which illustrates perspective views of a frame 100 with the lumen omitted for clarity, an angle a-b is defined between a plane formed by the circumference of hoop structure 100a and a plane formed by the circumference of hoop structure 100b. Similarly, an angle b-c is defined between hoop structure 100b and hoop structure 100c, and an angle c-d is defined between hoop structure 100c and hoop structure 100d.

In some embodiments, an angle between a pair of coupled hoop structures can be dependent upon the diameter of each coupled hoop structure. In an example, the diameter of hoop structure 100a can be greater than the diameter of hoop structure 100b, and the diameter of hoop structure 100b can be greater than the diameter of hoop structure 100c. Hoop structure 100a can be coupled to a circumference of hoop structure 100b, and hoop structure 100c can be coupled to a circumference of hoop structure 100b that can be opposite of hoop structure 100a. When positioned within a lumen 20 having a diameter that is less than the diameter of hoop structure 100c, an angle a-b between hoop structure 100a and hoop structure 100b can be greater than an angle b-c between hoop structure 100b and hoop structure 100c.

Figure 4:
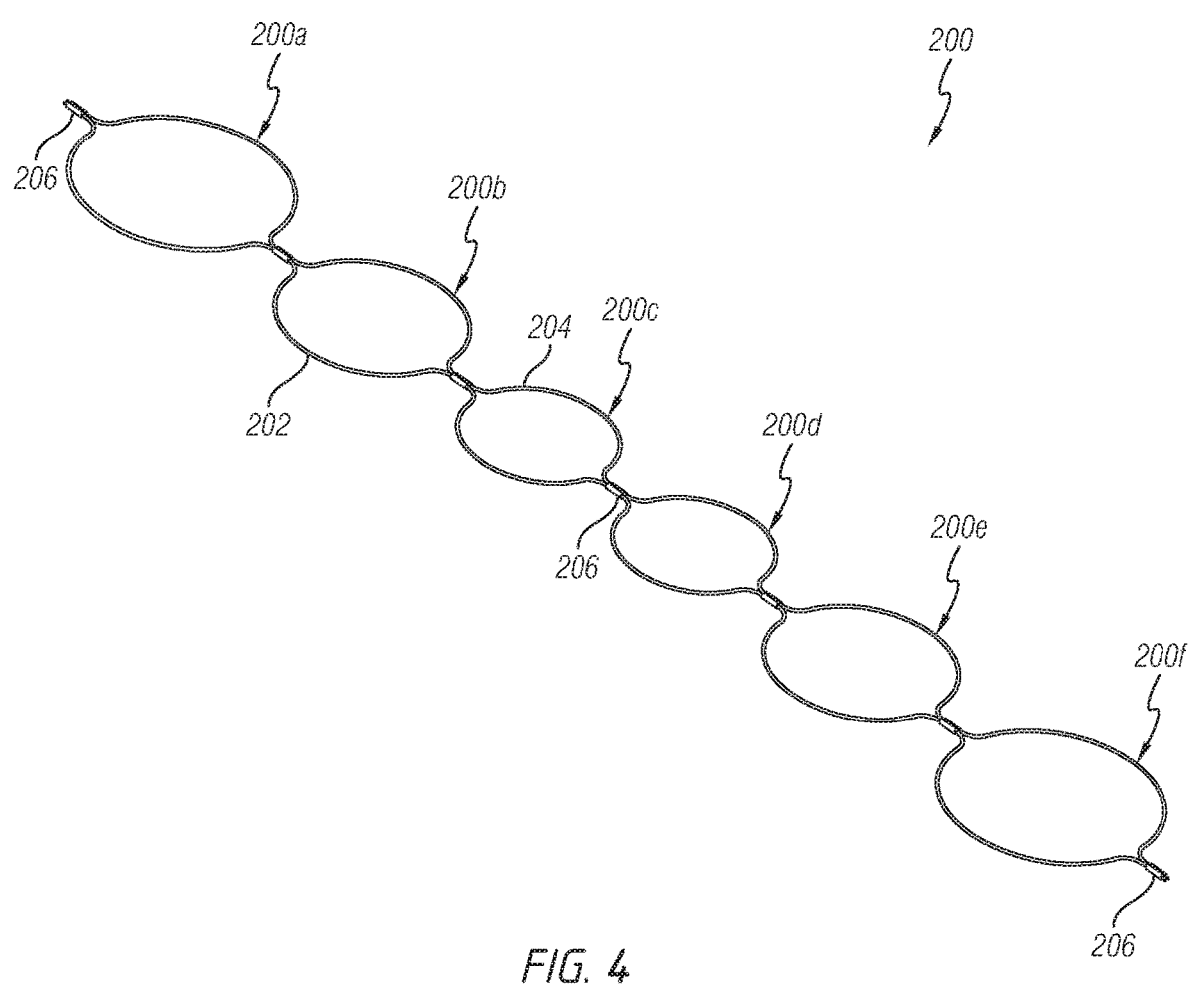
FIG. 4 illustrates a perspective view of an occlusive implant, according to some embodiments.

Referring now to FIG. 4, a perspective view of an occlusive implant frame 200 is illustrated. In some embodiments, the frame 200 can comprise a first elongate wire 202 and a second elongate wire 204. In a the collapsed configuration, the first and second elongate wires 202 and 204 extend parallel to each other along a longitudinal axis 2. In the collapsed or elongated into a substantially linear configuration, adjacent hoop structures extend in a substantially linear configuration along the longitudinal axis, and in an expanded configuration, the adjacent hoop structures extend transverse relative to the longitudinal axis 2.

The first elongate wire 202 and the second elongate wire 204 are coupled together at a plurality of positions along the axis 2 to interconnect the first and second wires 202 and 204 and longitudinally secure the first and second wires 202 and 204 relative to each other. In some embodiments illustrated in FIG. 4, the first and second wires 202 and 204 can optionally be coupled together by one or more collar 206. In some embodiments, the one or more collar 206 can be a hypotube or other cylindrical structure configured to retain the first and second wires 202 and 204 together. In some embodiments, the one or more collar can be crimped or compressed with the first and second wires 202 and 204 extending through the one or more collar 206.

In an expanded configuration in which the first and second wires 202 and 204 are resiliently spaced apart from each other, the first and second wires 202 and 204 form a hoop structure between a pair of adjacent positions where first elongate wire 202 is coupled to the second elongate wire 204. The hoop structure can have a rounded shape in the expanded configuration. In some embodiments, the hoop structure can have a circular shape in the expanded configuration. In some embodiments, the first and second wires 202 and 204 can form at least four, five, six, seven, eight, nine, ten, or more hoop structures. In some embodiments, like the example embodiments illustrated in FIGS. 1-6, the first and second wires 202 and 204 form six hoop structures 200a through 200f. In an example, the hoop structures 200a-200f are formed between a plurality of collars 206 when the first and second elongate wires 202 and 204 are spaced apart from each other.

Figure 5:
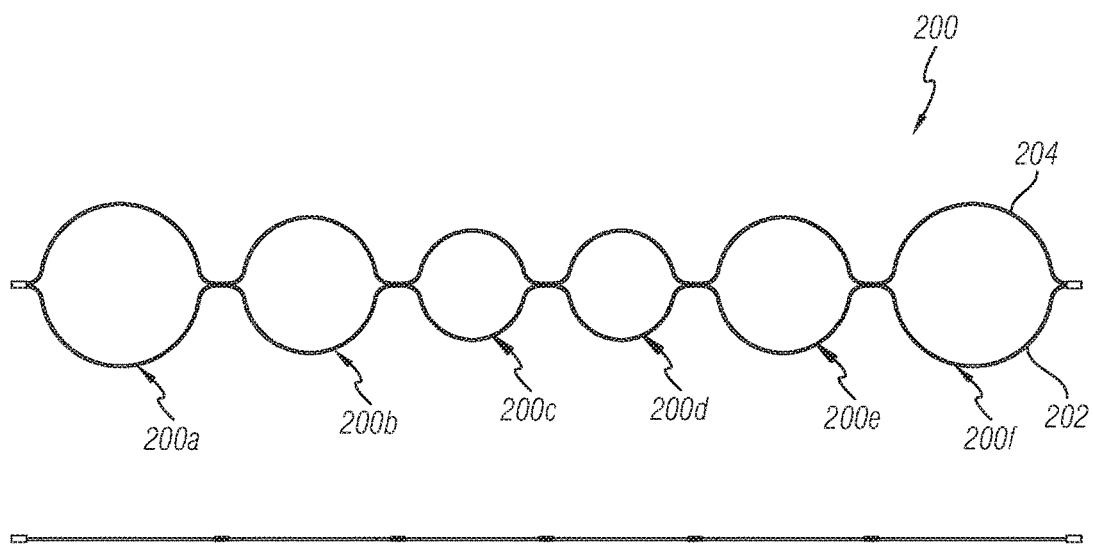
FIG. 5 illustrates a top plan and side elevation view of an occlusive implant, according to some embodiments.

FIG. 5 illustrates a top plan view and a side elevation view of an occlusive implant frame 200. The frame 200 can comprise a first elongate wire 202 and a second elongate wire 204 that optionally form hoop structures between a first end and a second end opposite the first end. In an example, the frame can comprise a pair of outer hoop structures 200a and 200f positioned at the first and second ends of the frame 200. Between the outer hoop structures 200a and 200f, the frame 200 may have a pair of intermediate hoop structures 200b and 200e. Between intermediate hoop structures 200b and 200e, the frame 200 may have a pair of center hoop structures 200c and 200d. In some configurations, the intermediate hoop structures 200b and 200e have a diameter that is less than the outer hoop structures 200a and 200f, and greater than the center hoop structures 200c and 200d. However, the arrangement and relative sizing of the structures can be varied, with smallest-sized hoop structures at the ends, largest-sized hoop structures in the middle, and intermediate-sized hoop structures positioned between the sets of smallest and largest-sized hoop structures. Further, although the frame is shown using sets of approximately equally sized hoop structures, the hoop structures can each have a unique size, different from that of other hoop structures of the frame.

In some embodiments, each of the first and second wires 202 and 204 has a diameter of 0.006 inch. The first elongate wire 202 and the second elongate wire 204 can be coupled together at a plurality of positions along a longitudinal length of the frame 200 to interconnect and secure the first and second wires 202 and 204 relative to each other.

Figure 7:
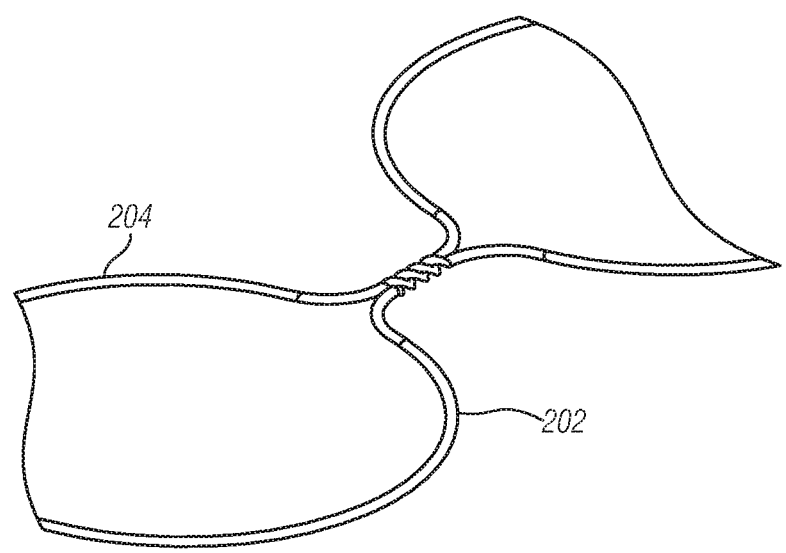
FIG. 7 illustrates a detail view of an occlusive implant, according to some embodiments.

For example, referring to the detail view of FIG. 7, the first elongate wire 202 and the second elongate wire 204 can be twisted about each other to interconnect the first and second wires 202 and 204 relative to each other. This unique configuration can interconnect the first and second elongate wires 202, 204 without requiring additional components, thus simplifying the assembly of the frame. Optionally, the first and second wires 202 and 204 can be interconnected at a plurality of positions along the longitudinal length of the frame 200.

Referring back to FIG. 5, the interconnected first and second wires 202 and 204 may have a cross-sectional width of 0.017 inch, a diameter of 0.011 inch, and a longitudinal length of 0.039 inch (1 mm). In some embodiments, the frame 200 has a longitudinal length of 2.870 inches in an expanded configuration. The outer hoop structures 200a and 200f may have a longitudinal length of 0.414 inch (10.5 mm). The intermediate hoop structures 200b and 200e may have a longitudinal length of 0.354 inch (9 mm). The center hoop structures 200c and 200d may have a longitudinal length of 0.295 inch (7.5 mm). In some embodiments, the frame 200 may form a radius 0.039 inch (1 mm) between each hoop structure.

Figure 6:
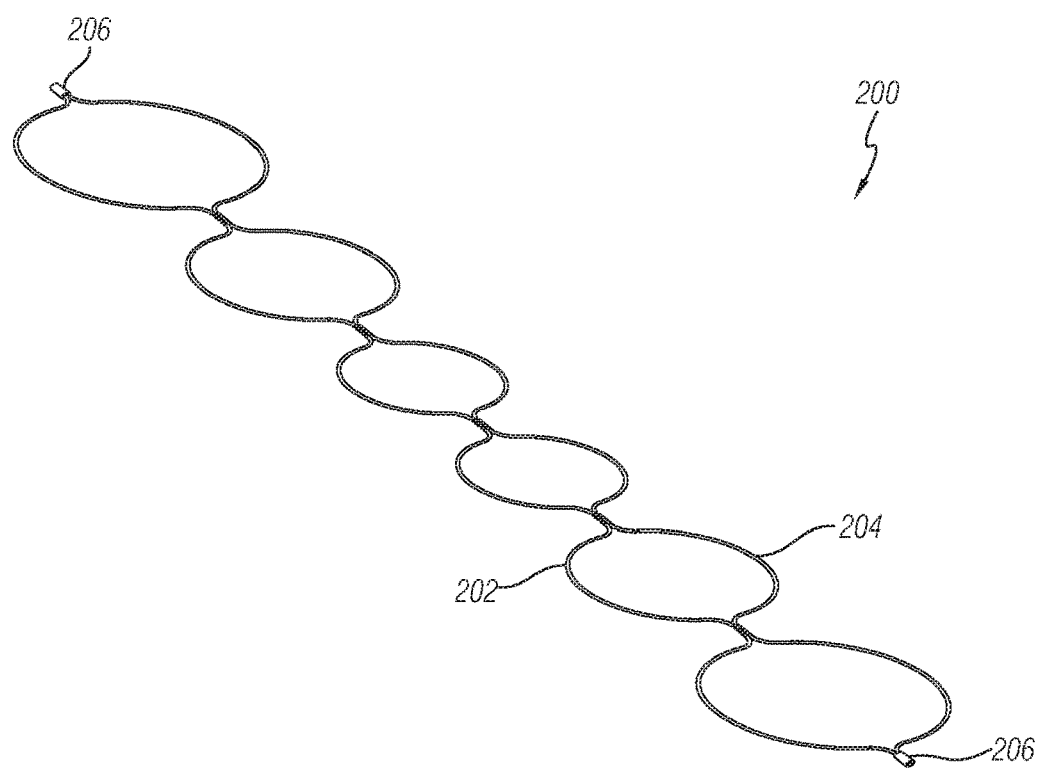
FIG. 6 illustrates a perspective view of an occlusive implant, according to some embodiments.

Referring to FIG. 6, the frame 200 is illustrated in an expanded configuration. A first elongate wire 202 and a second elongate wire 204 can be coupled together at a plurality of positions along the longitudinal length of the frame 200 to form the hoop structures. As shown, at opposing ends of the frame 200, the first and second wires 202 and 204 are coupled together by a collar 206. Between the ends of the frame 200, the first and second wires 202 and 204 can be twisted about each other at a plurality of positions, thereby forming hoop structures between the ends of the frame 200.

Figure 8:
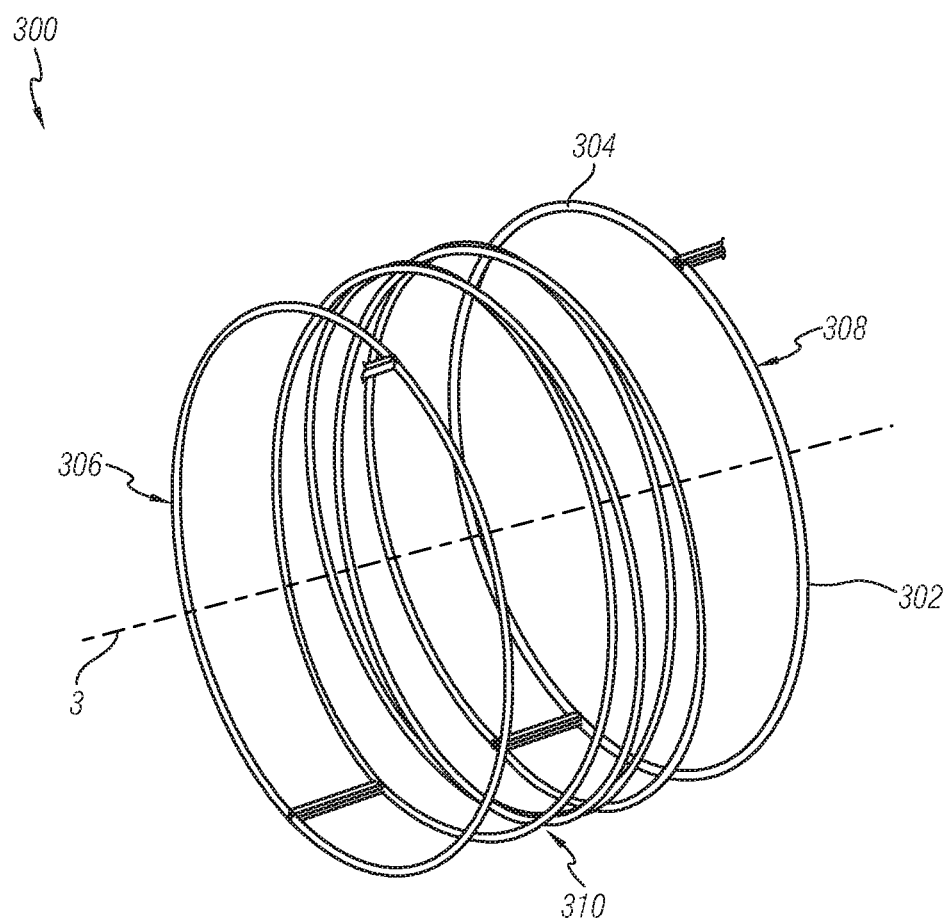
FIG. 8 illustrates a perspective view of an occlusive implant, according to some embodiments.

FIGS. 8-11 illustrate embodiments of the occlusive implant with a frame having one or more looped and/or helical sections. For example, FIG. 8 illustrates a frame 300 in an expanded configuration. The frame 300 has a first end and an opposing second end, and one or more loops or helical sections therebetween. In the expanded configuration, the frame 300 can form a tubular profile that has a variable diameter or a substantially cylindrical profile around an axis 3 that extends between the first and second ends. In accordance with some embodiments, the frame 300 can comprise a first partial or complete loop 306 at the first end thereof and a second partial or complete loop 308 at the second end thereof. Between the first and second loops, the frame can comprise a helical section 310 that extends between first and second loops 306 and 308.

For example, the first and second loops 306, 308 can extend along a circumference of the frame while the helical section 302 extends at an angle or in a helical direction relative to the first and second loops 306, 308. The first and second loops 306, 308 and the helical section 302 can be interconnected at opposing ends of the helical section 302. In some embodiments, the interconnection can be formed using a longitudinally extending coupling member that extends substantially parallel relative to the longitudinal axis 3. However, in some embodiments, the longitudinal coupling member can extend obliquely or at an angle relative to the longitudinal axis of the frame. The coupling member can have a length about equal to a length of the helical section 302 in its fully expanded state, as shown in FIGS. 9 and 10.

Figure 9:
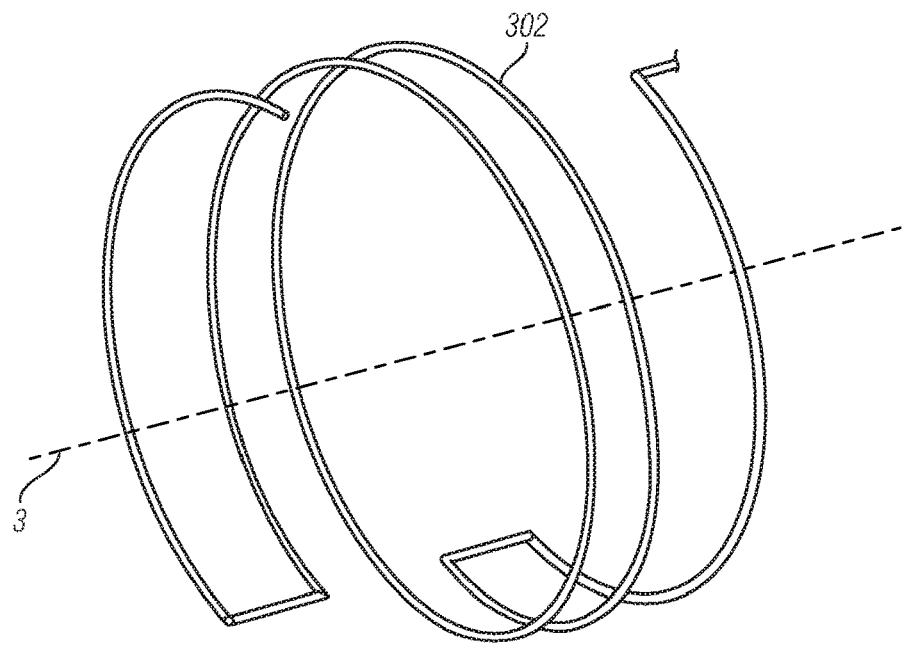
FIGS. 9 and 10 illustrate detail views of the occlusive implant of FIG. 8.
Figure 10:
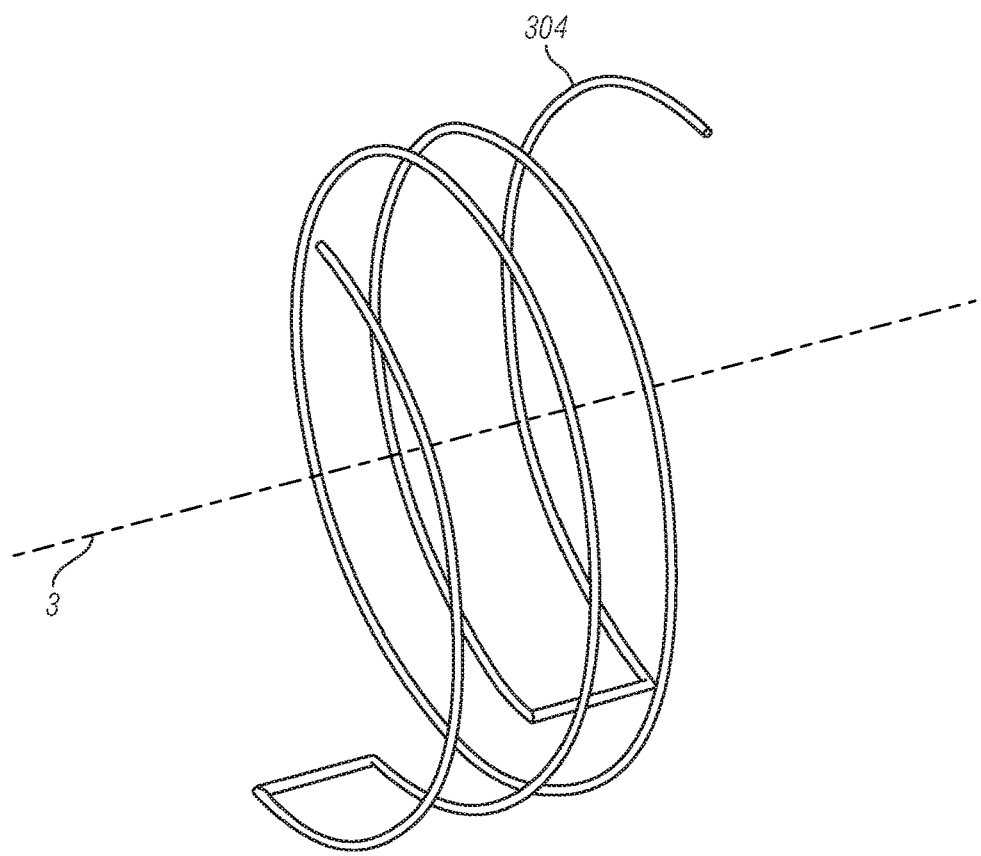
Figure 11:
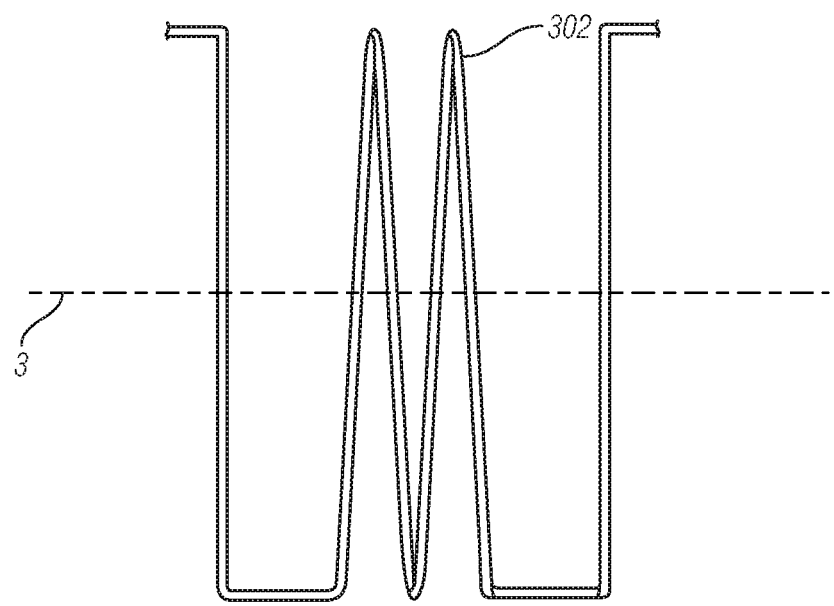
FIG. 11 illustrates a side detail view of the occlusive implant of FIG. 10.

Optionally, the frame 300 can comprise a first elongate wire 302 and a second elongate wire 304 coupled together along the longitudinal length of the frame 300 to form the one or more loops and/or helical sections, as shown in FIG. 8 (combining wires 302, 304 of FIGS. 9 and 10). In some embodiments of the present disclosure, the first and second elongate wires 302 and 304 can be coupled together by bonding or welding the wires. In some embodiments, the first and second elongate wires 302 and 304 can be twisted about each other to interconnect the wires.

When the frame 300 includes first and second elongate wires 302 and 304, as shown in FIG. 8, the first closed loop 306 can be formed by the first and second wires coupled to each other at a first location, the first and second wires diverging from the first location and converging toward each other at a second location to form the first closed loop. A helical section 310 can be formed adjacent to the first closed loop 306, the first wire 302 extending helically from the closed loop 306 in a first direction and the second wire extending helically from the closed loop 306 in a second direction, opposite the first direction, thereby forming the helical section 310. The second closed loop 308 can be formed opposite the first closed loop 306 with the helical section 310 disposed therebetween. The second closed loop 308 can be formed by the first and second wires coupled to each other at a third location adjacent to the helical section, the first and second wires diverging from the third location and converging toward each other at a fourth location to form the second closed loop.

Referring still to the frame 300, FIG. 9 illustrates the orientation of the first elongate wire 302 of the frame 300 (FIG. 8) in an expanded configuration. At a first end, the first elongate wire 302 extends from a first location around the axis 3 to a second location diametrically opposite the first location. At the second location, the wire first elongate wire 302 extends parallel to the axis 3 toward the second end. From the second location, the first elongate wire 302 extends around the axis 3 to a third location. In some embodiments, the first elongate wire 302 completes two spiral revolutions around the axis 3. At the third location, the first elongate wire 302 extends parallel to the axis 3 toward the second end. From the third location, the first elongate wire 302 extends around the axis 3 to a fourth location diametrically opposite the third location.

FIG. 9 illustrates the orientation of the second elongate wire 304 of the frame 300 in an expanded configuration. The second elongate wire 304 extends around the axis 3 and an opposite direction as that explained with regard to the first elongate wire 302. For clarity and brevity, an explanation of the orientation of second elongate wire 304 is omitted here.

Optionally, the frame forms a third loop at the first end of the frame. The third closed loop can be positioned such that the first closed loop can be interposed between the third closed loop and the helical section. The third closed loop can be formed by the first and second wires coupled to each other at a fifth location and diverging from the fifth location and converging towards the first location to form the third closed loop.

Optionally, the frame forms a fourth closed loop at the second end of the frame. The fourth closed loop can be positioned such that the second closed loop can be interposed between the fourth closed loop and the helical section. The fourth closed loop can be formed by the first and second wires diverging from the third location and converging toward each other at a sixth location to form the fourth closed loop.

It should be understood that the present disclosure is not limited to the embodiment of the frame 300 illustrated in FIGS. 8-11. For example, some embodiments of the frame can comprise a closed loop interposed between first and second helical sections. In yet another embodiment, a frame may be formed by first and second wires that converge to form a plurality of closed loops.

Figure 12:
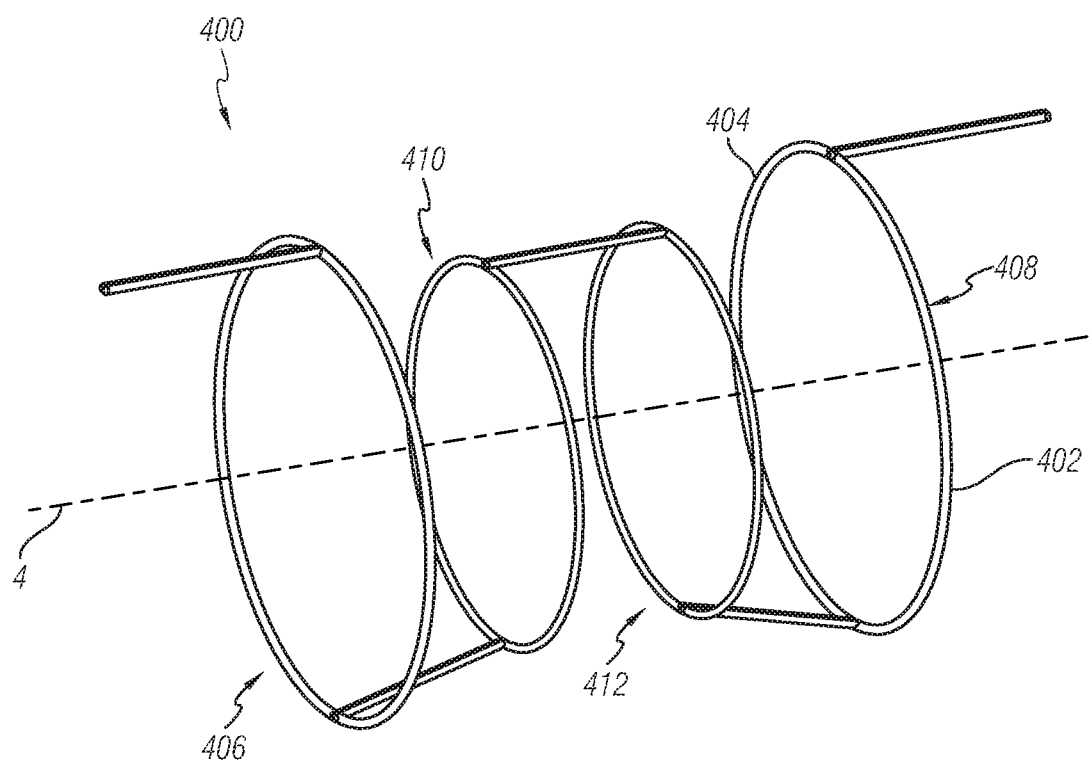
FIG. 12 illustrates a perspective view of an occlusive implant, according to some embodiments.
Figure 13:
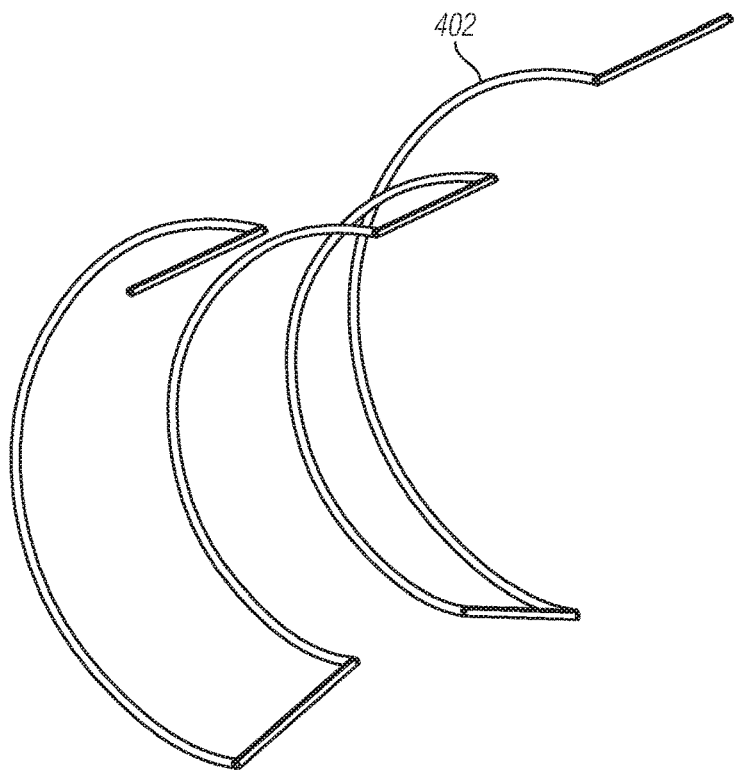
FIG. 13 illustrates a detail view of the occlusive implant of FIG. 12.
Figure 14:
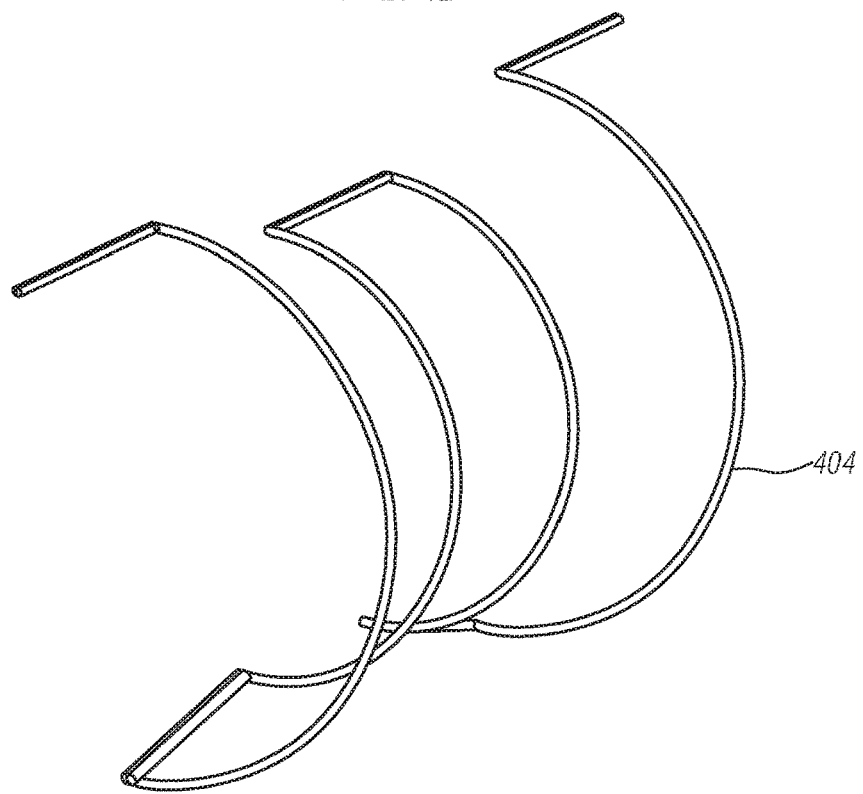
FIG. 14 illustrates a detail view of the occlusive implant of FIG. 12.

FIGS. 12-14 illustrate embodiments of the occlusive implant comprising a frame having closed loop sections.

Referring to FIG. 12, an example of an occlusive implant is illustrated having a frame 400 formed by first and second wires that converge to form the closed loops. The frame 400 has a first end and an opposing second end, and one or more closed loops therebetween. In the expanded configuration, the frame 400 forms a substantially cylindrical expanded profile around an axis 4 that extends between the first and second ends.

In some embodiments, the frame 400 can comprise a first elongate wire 402 and a second elongate wire 404 coupled together along the longitudinal length of the frame 400 to form the closed loop(s). In some embodiments of the present disclosure, the first and second elongate wires 402 and 404 can be coupled together by bonding or welding the wires. In some embodiments, the first and second elongate wires 402 and 404 can be twisted about each other to interconnect the wires.

The frame 400 may be formed as a first closed loop 406 at the first end of and a second closed loop 408 at the second end. Between the first and second closed loops, the frame can comprise one or more additional closed loops. For example, the frame 400 can comprise a third closed loop 410 and/or a fourth closed loop 412. In accordance with some embodiments, the first and second closed loops 106 and 408 can have the same or different diameter, and the third and fourth closed loops 410 and 412 have the same or different diameter. In some embodiments, all of the closed loops can have the same or different diameters.

Where the frame 400 can comprise first and second elongate wires 402 and 404, the first closed loop 406 can be formed by the first and second wires coupled to each other at a first location, then diverging from the first location, and converging toward each other at a second location to form the first closed loop. Each closed loop thereafter can be formed by the first and second elongate wires 402 and 404 diverging from each other at the location where the wires are coupled, and converging toward each other at the next location to form the next closed loop. In some embodiments, the portions of the frame 400, where the first and second elongate wires 402 and 404 are coupled, extends parallel to the axis 4.

FIG. 13 illustrates the orientation of the first elongate wire 402 of the frame 400 (FIG. 12) in an expanded configuration. At a first end, the first elongate wire 402 extends from a first location around the axis 4 to a second location diametrically opposite the first location. At the second location, the wire first elongate wire 402 extends parallel to the axis toward the second end. From the second location, the first elongate wire 402 extends around the axis to a third location. In some embodiments, the first elongate wire 402 extends around the axis to a third location and then extends back around the axis to a fourth location.

FIG. 14 illustrates the orientation of the second elongate wire 404 of the frame 400 in an expanded configuration. The second elongate wire 404 extends around the axis 4 and an opposite direction as that explained with regard to the first elongate wire 402. For clarity and brevity, an explanation of the orientation of second elongate wire 304 is omitted here. The wires 402, 404 can comprise longitudinal coupling members that interconnect the loops thereof. The longitudinal coupling members can be oriented parallel relative to the longitudinal axis of the frame. However, in some embodiments such as that shown in FIGS. 12-14, the longitudinal coupling member can extend obliquely or at an angle relative to the longitudinal axis of the frame.

In forming the frame 200, 300, 400 or others disclosed herein, the individual wires can be shaped or heat set into a curvilinear configuration before and/or after being joined with a corresponding wire to create the respective frame configuration. The wires (whether coupled together to form the frame or individually) can comprise a metal or polymer material, and can be heat set, molded, or otherwise shaped to have a resilient, self-expanding, bistable, and/or expandable shape. The frames can be self-expandable or balloon expandable.

Figure 48:
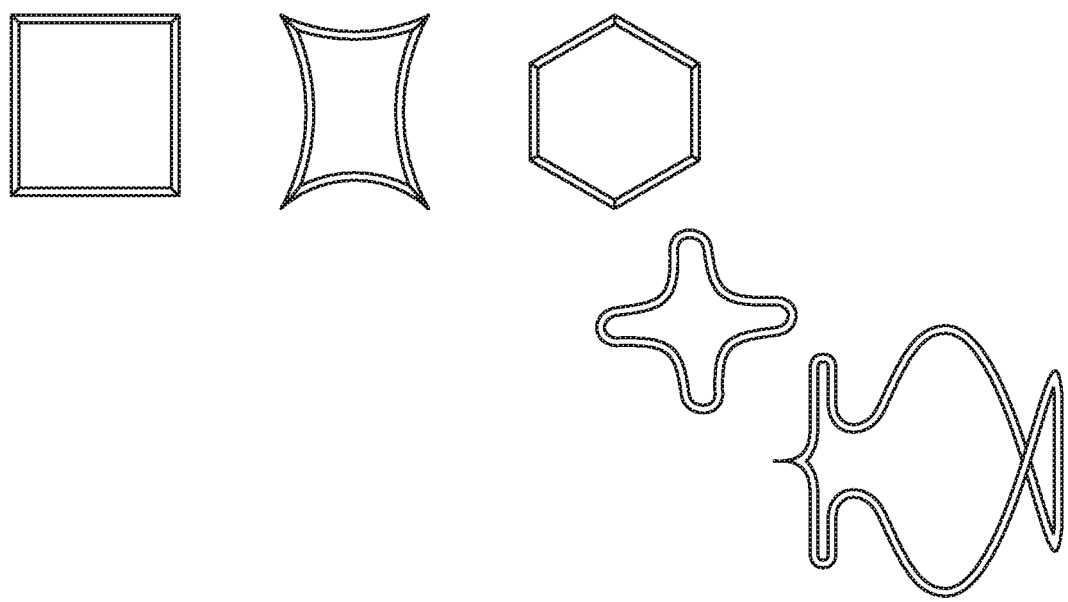
FIG. 48 illustrates side section views of an occlusive implant, according to some embodiments.

Although embodiments of the present disclosure include a frame having a cylindrical profile in an expanded configuration, some embodiments include a frame having other shape profiles. For example, referring to FIG. 48, the frame may have a cross-sectional profile with a regular or irregular shape, such as a square, pentagon, hexagon, cross, triangle, or some other shape having concave or convex portions or sharp or rounded edges relative to a longitudinal axis. Further, instead of or in combination with the generally round or oval-shaped hoop structures disclosed herein, the shapes shown in FIG. 48 can be employed in any of the implant embodiments disclosed herein.

Delivery Systems

In accordance with some embodiments, a delivery system is provided that can control release and expansion of the implant at a target site within a lumen of a vasculature. The delivery system may comprise an implant carrier assembly with an occlusive implant retained therein. The implant carrier assembly can be inserted into a lumen where the occlusive implant can be positioned. The occlusive implant can then be deployed and released from the implant carrier assembly and permitted to expand within the lumen.

Figure 15:
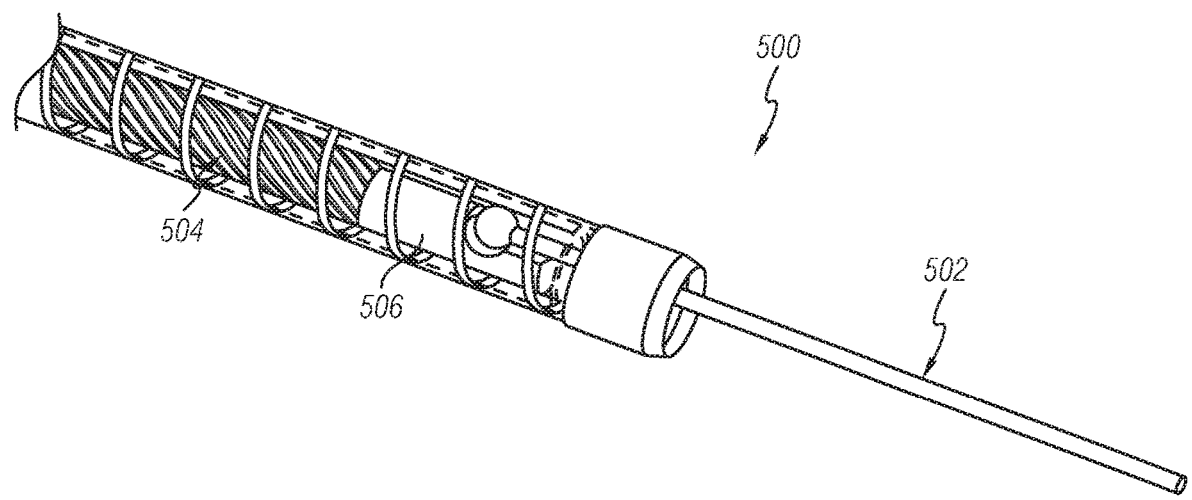
FIG. 15 illustrates a perspective view of an implant carrier assembly, according to some embodiments.
Figure 16:
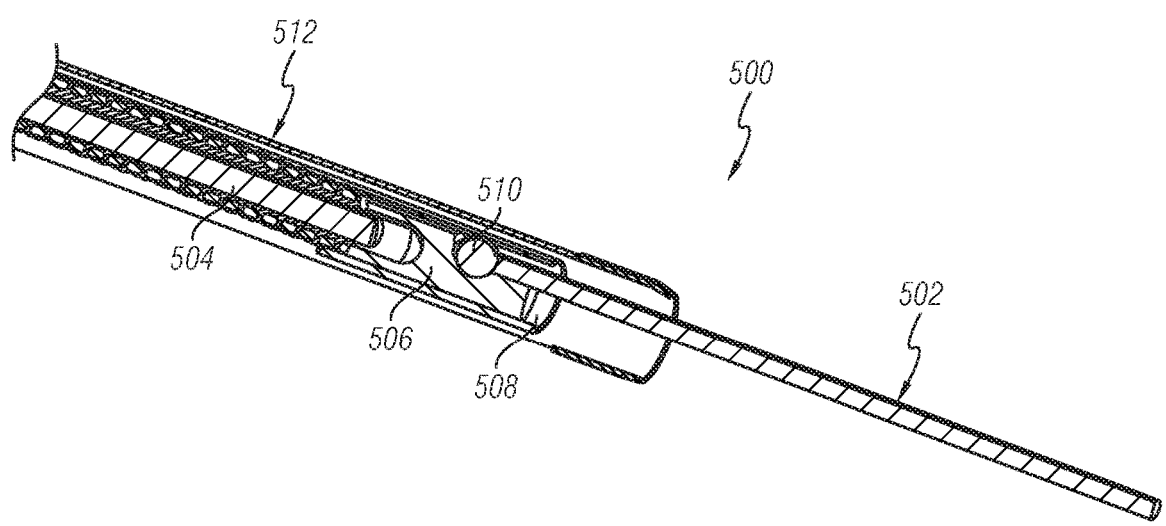
FIG. 16 illustrates a perspective section view of an implant carrier assembly, according to some embodiments.
Figure 17:
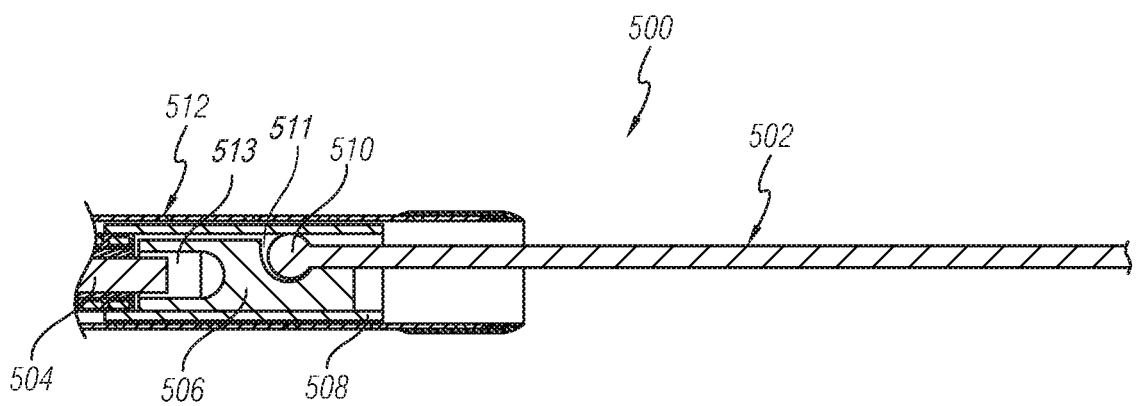
FIGS. 17-20 illustrate section views of an implant carrier assembly, according to some embodiments.
Figure 18:
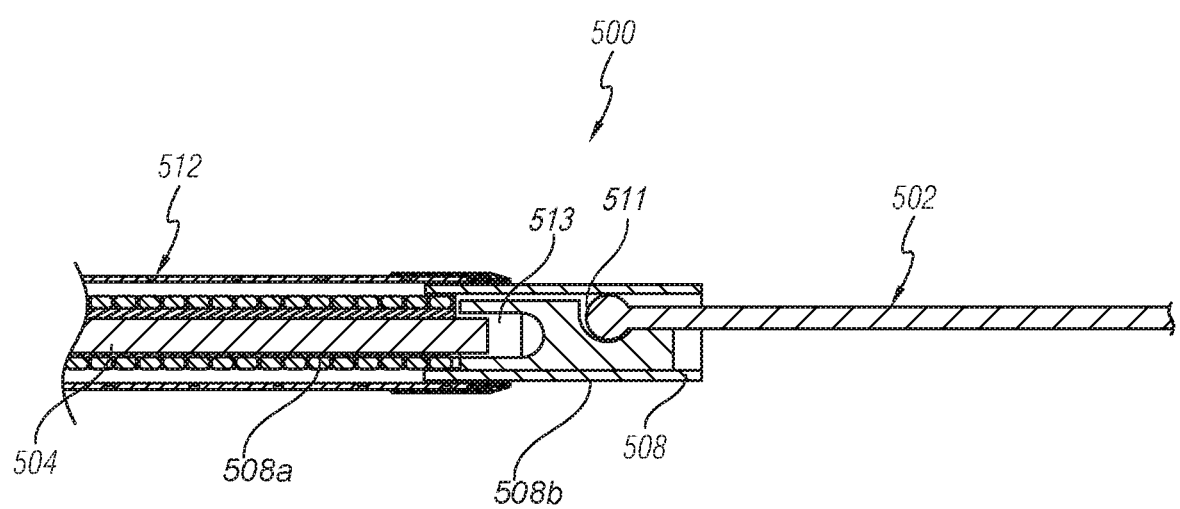

For example, FIGS. 15-21 illustrate embodiments of an implant carrier assembly and an occlusive implant. Referring to FIGS. 15-16, an implant carrier assembly 500 can comprise an engagement member 504 having a distal end portion with a socket 506. The socket 506 can be configured to retain the occlusive implant 502 within the implant carrier assembly 500. In some embodiments, the implant carrier assembly 500 can comprise a sheath 508 such that a portion of the occlusive implant 502 can be constrained within or retained between the socket 506 and the sheath 508. In some embodiments (as shown in FIG. 18), the engagement member 504 comprises a slotted hypotube 508a and a distal band 508b, the hypotube 508a having inner and outer diameters, the band 508b having an inner diameter equal to or greater than the hypotube 508a outer diameter and an outer profile of the engagement member 504 distal end portion to permit the engagement member distal end portion to be slidably receivable within the band 508b.

In some embodiments, the implant carrier assembly 500 can comprise a catheter 512 having a lumen that extends between a proximal portion and a distal portion thereof, and the engagement member 504 and sheath 508 can be retained within the lumen of the catheter 512. The lumen of the catheter 512 can be configured to permit the distal end portion of the sheath 508 to be movable within the lumen proximal to or distal to the distal portion of the catheter 512.

Referring to FIG. 16, the socket 506 can extend from an outer surface of the distal end portion of the engagement member 504. A distal end portion of the socket can comprise a void having an inner profile with a cross-sectional length that is greater than an outer profile of the occlusive implant 502. In some embodiments, the socket 506 extends from distal end portion into the engagement member 504.

In some embodiments, the socket 506 can be formed separately from the engagement member 504 and coupled to the engagement member 504. Such an embodiment as illustrated in FIGS. 15-16.

The distal end portion of the socket 506 can include a first void or engagement cavity 511 extending proximally toward the engagement member 504. In some embodiments, the first void 511 extends a first depth into the socket 506. A second void or proximal connection cavity 513 extends into a proximal end of the socket 506 towards the distal end. In some embodiments, the second void 513 extends a second depth into the socket distally towards the first void 511. In some embodiments, the second depth can be less than the first depth.

FIG. 17 illustrates a side section view of a proximal portion, wire(s), or connecting portion of an occlusive implant 502 engaged with the implant carrier assembly 500. The engagement member 504 is positioned within the sheath 508 such that a distal end portion of the socket 506 is aligned with a distal end portion of the sheath 508. The distal end portion of the sheath 508 is aligned with or proximal to a distal end portion of the catheter 512.

In some embodiments, the first void has a first cross-sectional width along a first portion proximal to the distal end of the socket 506, and a second cross-sectional width along a second portion that is proximal to the first portion, wherein the second cross-sectional width is greater than the first cross-sectional width.

The first void is configured to receive, engage, and/or restrain a proximal portion of the occlusive implant 502 within the implant carrier assembly 500. In a restricted position, the proximal portion of the occlusive implant 502 is positioned in the first void between the socket 506 at and an inner surface of the sheath 508.

In some embodiments, the proximal portion of the occlusive implant 502 can comprise a proximal coupling member 510. The proximal coupling member 510 can comprise an outer profile having a cross-sectional width or profile that can be greater than a cross-sectional sectional profile of the wire(s) or connecting portion of the frame width at the proximal portion of the occlusive implant 502. In some embodiments, the proximal coupling member 510 can comprise a sphere extending from an outer surface of the frame. The first void can comprise an inner profile that generally mates with, couples to, matches approximates, or is equal to or larger than an outer profile of the proximal coupling member 510 to permit the proximal coupling member 510 to be positioned within the socket. However, as illustrated, the outer profile of the proximal coupling member 510 can also be greater than the cross-sectional space created between the width, depth, or profile of the second void of the socket 506 and an inner surface of the sheath 508. Thus, the proximal coupling member 510 can be seated into the socket 506; however, because the proximal coupling member 510 cannot be passed distally beyond the second void of the socket 506, the proximal coupling member 510 can be retained or captured between the second portion of the socket 506 and the sheath 508 to collectively restrict longitudinal movement of the occlusive implant 502 out of the socket 506. This capturing or restrained will be maintained until the sheath 508 (or other sleeve used in addition to or in place of the sheath 508, such as the catheter 512, in some embodiments) is proximally retracted relative to the socket 506, thus exposing the proximal coupling member 510 and permitting the proximal coupling member 510 to separate from the first void of the socket 506.

Referring now to FIG. 18, to direct the occlusive implant 502 out of the implant carrier assembly 500, and permit the occlusive implant 502 to move into an expanded configuration, the engagement member 504 and sheath 508 are directed toward a distal end portion of the catheter 512. The engagement member 504 (which can be advanced as a unit with the sheath 508) can be advanced distally relative to the catheter 512 (whether the engagement member 504 or the catheter 512 is maintained stationary) such that the first void of the socket 506 exits the catheter lumen and is positioned distal to the distal end of the catheter 512. Because the sheath 508 is also positioned distal to the distal end of the catheter 512, the proximal coupling member 510 remains in the restricted position, retained between the socket 506 and sheath 508.

Figure 19:
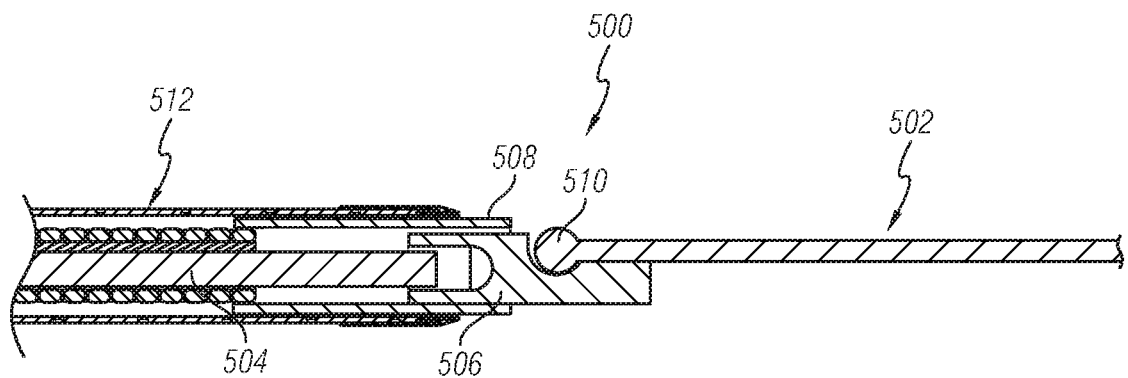
Figure 20:
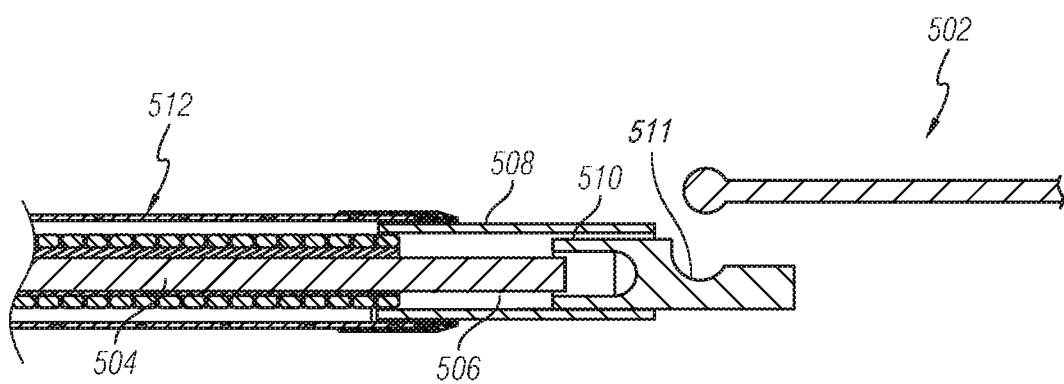

Referring to FIG. 19, the occlusive implant 502 can be released from the implant carrier assembly 500 by moving the sheath 508 relative to the socket 506 such that the sheath 508 is positioned proximal to the distal end of the engagement member 504 and the socket 506 is positioned distal to the sheath 508 distal end. With the socket 506 positioned distal to the sheath 508, the occlusive implant 502 is no longer restrained and the proximal coupling member 510 is permitted to exit the socket 506. FIG. 20 illustrates in an example of the occlusive implant 502 released from the implant carrier assembly 500.

The implant carrier assembly 500, in some embodiments, can comprise a handle assembly. The handle assembly can include a first slidable member and a second slidable member. The first slidable member can be coupled to a proximal end of the engagement member 504, and the second slidable member can be coupled to a proximal end of the sheath 508. The first and second slidable members can have a first configuration in which the first and second slidable members are coupled together. In the first configuration, the first and second slidable members can move in unison together as a single unit. For example, the first and second slidable members may be advanced through the catheter 512 such that a portion of the engagement member 504 and sheath 508 extend distal to the distal end of the catheter 512, as illustrated in FIG. 17. In a second configuration of the first and second slidable members, the first and second slidable members can be movable relative to each other. In the second configuration, the engagement member 504 can be permitted to be moved relative to the sheath 508. For example, the second slidable member may be retracted to direct the sheath 508 proximal to the first void of the socket 506.

Figure 21:
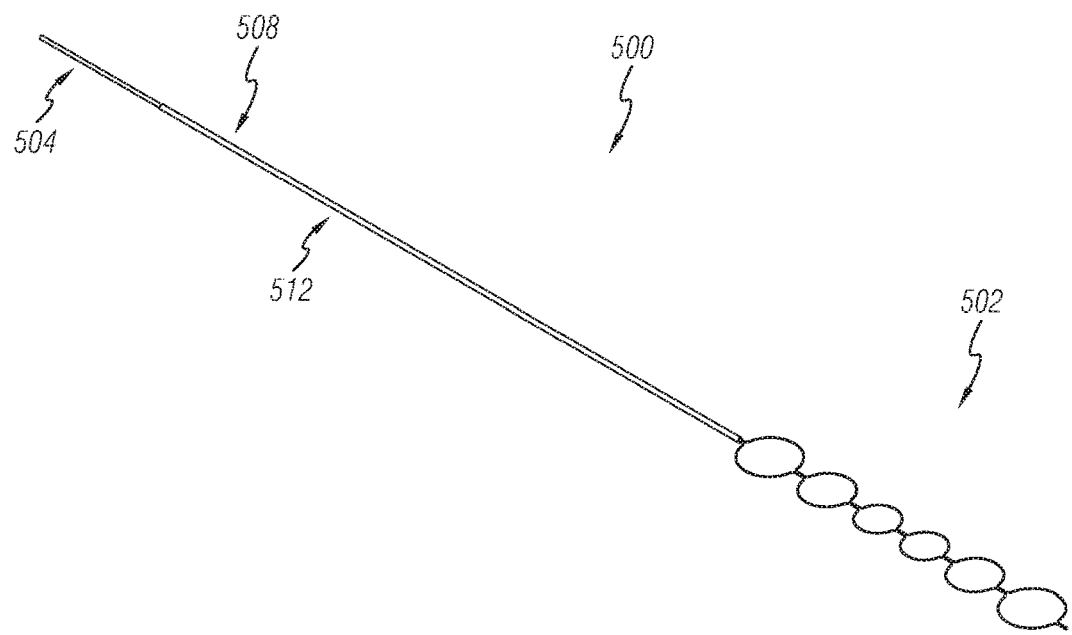
FIG. 21 illustrates a perspective view of an implant carrier assembly, according to some embodiments.
Figure 22:
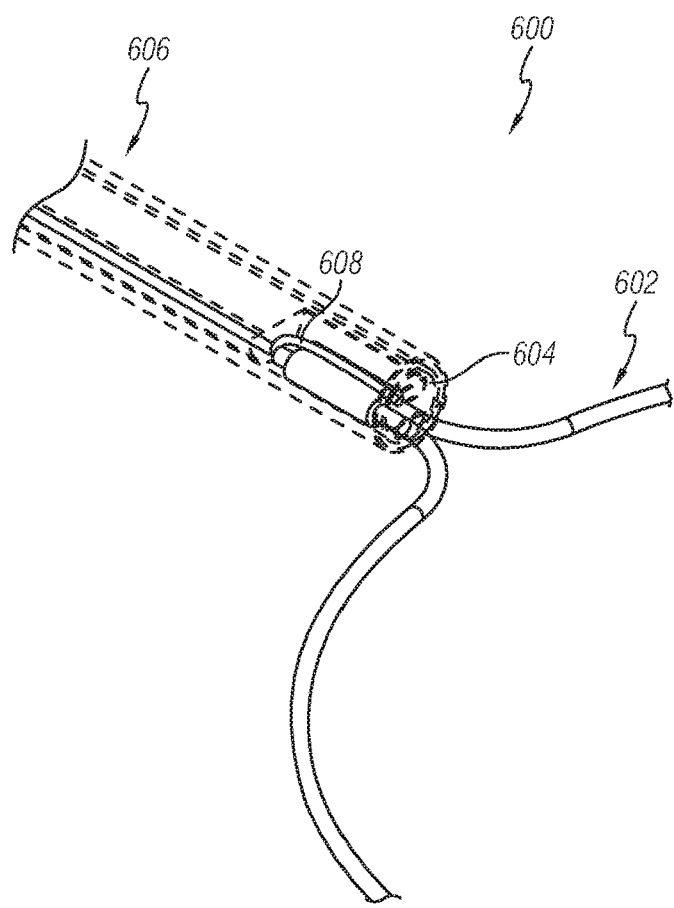
FIG. 22 illustrates a perspective detail view of an implant carrier assembly, according to some embodiments.

FIG. 21 illustrates an occlusive implant 502 coupled to an implant carrier assembly 500. The implant 502 can be initially prepared for implantation into a body lumen by positioning the implant 502 within a lumen of the catheter 512. In order to do so, the proximal coupling member 510 can be interconnected with the socket 506 and the sheath 508 can be advanced over the socket and the proximal coupling member 510 to capture the proximal coupling member 510 within the first void of the socket 506. Thereafter, the sheath 508 and the engagement member 504 can be proximally retracted into the lumen of the catheter 512, pulling the implant 502 proximally into the lumen of the catheter 512. As this occurs, the implant 502 will assume a collapsed configuration, in which the implant 502 has a generally linear configuration, whose maximum cross-sectional profile is approximately the sum of the cross-sectional profiles of the wires of the implant 502, which allows the size of the catheter 512 to be minimized, as discussed herein. Accordingly, the implant 502 can thus be loaded into the catheter 512 and readied for implantation into the body lumen.

As discussed with respect to FIGS. 17-20 above, the implant 502 can be expanded and then released at a target site within a body lumen through relative movement of the engagement element 504, the sheath 508, and the catheter 512. To expand the implant 502, the engagement element 504 and the sheath 508 can be advanced distally relative to the catheter 512, thus urging the implant 502 out of the lumen of the catheter 512. The implant 502 can expand, section by section, allowing the clinician to verify and adjust the placement of the implant 502 as needed. Should the implant 502 need to be re-positioned, the clinician can recapture or resheath the implant 502 by distally advancing the catheter 512 relative to the engagement element 504 and the sheath 508, which polls the implant 502 into the lumen of the catheter 512 and collapses the implant 502 into its collapsed state. The implant 502 can then be repositioned within the body lumen and the expansion process can be restarted. Due to the significant expansion of the implant 502 relative to its collapsed cross-sectional profile, and considering that the length of the occlusive implant 502 in the collapsed configuration is greater than the length of the occlusive implant 502 in the expanded configuration, the clinician can distally advance the engagement element 504 and the sheath as the implant 502 expands within the body lumen. After the implant 502 is fully expanded within the body lumen and the socket 506 is positioned distally relative to the distal end of the catheter 512, the sheath 508 can be proximally retracted relative to the socket 506, thereby releasing the proximal coupling member 510 from engagement with the socket 506. This final movement results in disengagement of the implant carrier assembly 500 from the implant 502 and the implantation is complete. In accordance with some embodiments, additional procedures can be performed, such as implanting embolic material or eventually restoring flow by removing the implant 502 or puncturing a membrane coupled to the implant 502, as discussed herein and in the various applications Incorporated herein by reference.

FIGS. 22-25 illustrate embodiments of an implant carrier assembly 600 and an occlusive implant 602. The implant carrier assembly 600 can comprise an engagement member 604 having a distal end portion with a socket and an ejection wire 608. In some embodiments, the engagement member 604 can be positioned within a catheter 606 having a lumen that extends between a proximal end and a distal end. The lumen of the catheter 606 can be configured to permit the engagement member 604 to be movable within the lumen relative to the proximal and distal ends.

Figure 23:
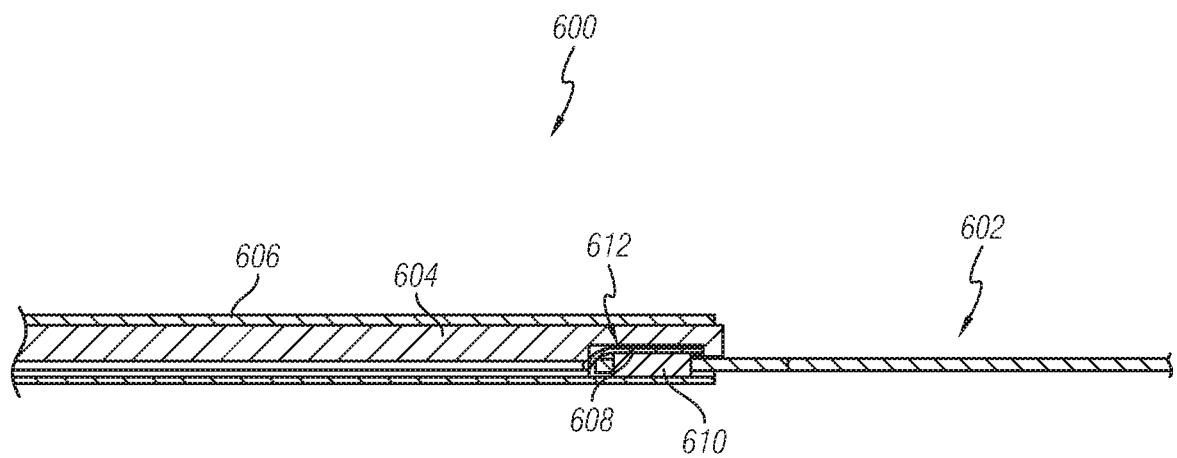
FIGS. 23-25 illustrate section views of an implant carrier assembly, according to some embodiments.

FIG. 23 illustrates a side section view of an implant carrier assembly 600 and an occlusive implant 602 coupled thereto. In a restricted position, the engagement member 604 is positioned within the catheter 606 such that a distal end of the engagement member 604 is aligned with or position proximal to a distal end of the catheter 606 such that a socket 612 of the engagement member 604 is disposed within the lumen of the catheter 606. The socket 612 can extend into the distal end portion of the engagement member 604 and share features similar to those discussed above with respect to the socket 506, details of which will not be repeated herein for brevity but are incorporated here by reference. In some embodiments, the socket 612 extends transverse to a longitudinal axis of the engagement member 604.

The carrier assembly can comprise an ejection component that extends within or along the socket and can be used to facilitate disengagement between the implant and the socket. An ejection component can be beneficial to ensure that the implant is fully disengaged from the carrier assembly. The ejection component can comprise a flexible, elastic, or resilient material that can be manually or self-actuated in order to create separation between the carrier assembly and the coupling of the implant, in order to separate the implant from the carrier assembly. In some embodiments, the ejection component can comprise a wire or a resilient compressible pad that can be coupled to or extend across at least a portion of the socket, and in some embodiments, be coupled to or extend across at least a portion of the void of the socket. Further, the ejection component can be manually actuated by pushing or pulling the ejection component relative to the socket.

For example, as illustrated in FIG. 23, the carrier assembly 600 can comprise an ejection wire 608 that can extend within the void of the socket 612. A distal end of the ejection wire 608 can be coupled to a distal segment of the socket, and a proximal end of the ejection wire 608 can be movable and actuatable by the clinician. The ejection wire 608 can be interposed between the proximal portion of the occlusive implant 602 and the catheter 606. The ejection wire 608 may have a recessed configuration and an ejection configuration.

In the recessed configuration, the ejection wire 608 can be slack and extend along a bottom surface of the socket 612. In the recessed configuration, the ejection wire 608 permits the proximal portion of the occlusive implant 602 to be positioned in the socket 612. For example, referring to FIG. 23, in the restricted position, the proximal portion of the occlusive implant 602 can be interposed or engaged between the socket 612 and an inner surface of the catheter 606 with the ejection wire 608 interposed between the proximal portion of the occlusive implant 602 and the surface of the void of the socket 612.

Figure 24:
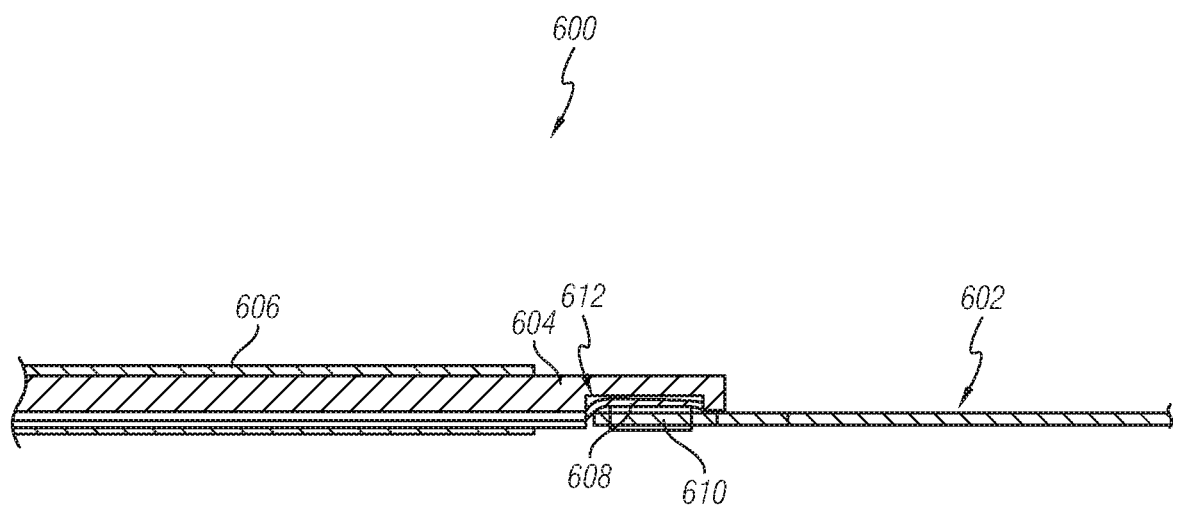
Figure 25:
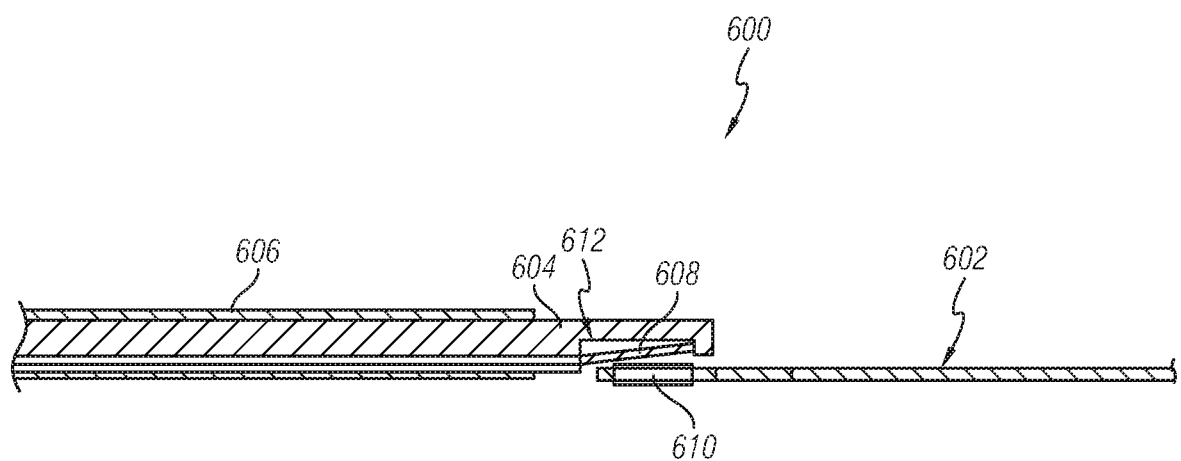

After the implant 602 has been positioned within a body lumen and expanded as discussed above with regard to FIGS. 15-21, the occlusive implant 602 can be released. The use of the ejection wire 608 facilitates full disengagement of the implant 602 from the carrier assembly once the implant 602 has been initially released by proximally retracting the sheath relative to the socket to expose the proximal portion of the implant 602, as illustrated in FIG. 24. Thereafter, as illustrated in FIG. 25, the ejection wire 608 can be moved to the ejection configuration, for example, by pulling the ejection wire 608 proximally relative to the socket 612. In the ejection configuration, slack is removed from the ejection wire 608 so that it becomes taut and moves upwardly and away from the surface of the void of the socket 612 to extend transversely across the socket 612. The movement of the ejection wire 608 to the ejection configuration, e.g., from slack to taut, urges the occlusive implant 602 out of the socket 612.

As noted above, in some embodiments, the ejection wire 608 can be a flexible line that can be coupled to the distal end of the engagement member 604 and extends from the socket 612 toward a proximal end of the implant carrier assembly 600. A proximal portion of the ejection wire 608 may extend through a passage in the engagement member 604 or catheter. For example, in some embodiments, the ejection wire 608 can extend from the socket 612 between an outer surface of the engagement member 604 and an inner surface of the lumen of the catheter 606 or within a separate lumen of the catheter 606. In some embodiments, the ejection wire 608 can extend proximally to and be coupled to an ejection actuator of a handle assembly. The ejection actuator can enable a clinician to manually actuate the ejection wire 608, thereby causing the ejection wire to move to the ejection configuration, e.g., from slack to taut.

In some embodiments in which the ejection component comprises a self-actuating member, the occlusive implant 602 can be automatically released from the implant carrier device 600 when the socket 612 is positioned distal to the distal end of the catheter 606. For example, the ejection wire 608 may comprise a resilient resiliently flexible material that extends transversely across a portion of the socket 612 in a recessed configuration. When the occlusive implant 602 is positioned between the socket 612 an inner surface of the catheter 606 (e.g., FIG. 23), the ejection wire 608 can be resiliently displaced (for example, away from the ejection configuration to the recessed configuration). However, when the socket 612 is positioned distal to the distal end of the catheter 606, the force of the resilient ejection wire 608 is no longer restrained by the catheter 606 (or sheath, in some embodiments), and therefore, the self-actuating a resilient ejection wire 608 moves to urge the proximal portion of the occlusive implant 602 away from the socket 612.

Accordingly, in some embodiments, the ejection wire can comprise a shape memory material. For example, the shape memory material permits the occlusive implant 602 to displace the ejection wire 608 in an ejection or deactivated configuration. However, when the shape memory material is activated (e.g., when compressive forces from the catheter or sheath are removed) or self-actuated, the ejection wire can expand or move away from an inner surface of the socket and urge the occlusive implant 602 out of the socket 612.

Further, although the ejection component is discussed as being an elongate wire in the illustrated embodiments, the ejection component can comprise a short wire or band coupled to the proximal and distal ends of the socket itself, one or more cantilevered tabs or flaps that are coupled to a perimeter of the void of the socket and have free, resilient ends extending into the void that are biased toward an ejection configuration, and/or other self-expanding, resilient, or elastic components.

FIGS. 26-33 illustrate an embodiment of an implant carrier assembly configured to releasably engage with an occlusive implant. In some embodiments, the implant carrier assembly can comprise a core member with a release component, movable relative to the core member, configured to engage and retain an occlusive implant in an engaged position, and to release an occlusive implant in a released position. The release component can comprise a wire, hook, tab, or loop that can engage with a proximal portion of an implant and be manually or automatically actuated to disengage from the implant when a condition is met. The release component can extend through a lumen of the carrier assembly or be coupled to the distal portion of the carrier assembly. The condition can include, for example, distal advancement of the release component beyond an end of a catheter in which the carrier assembly is housed, proximal retraction of a sheath relative to the distal end portion of the carrier assembly, or user actuation. Once the conditions met, the implant can be released from engagement with the release component.

Figure 26:
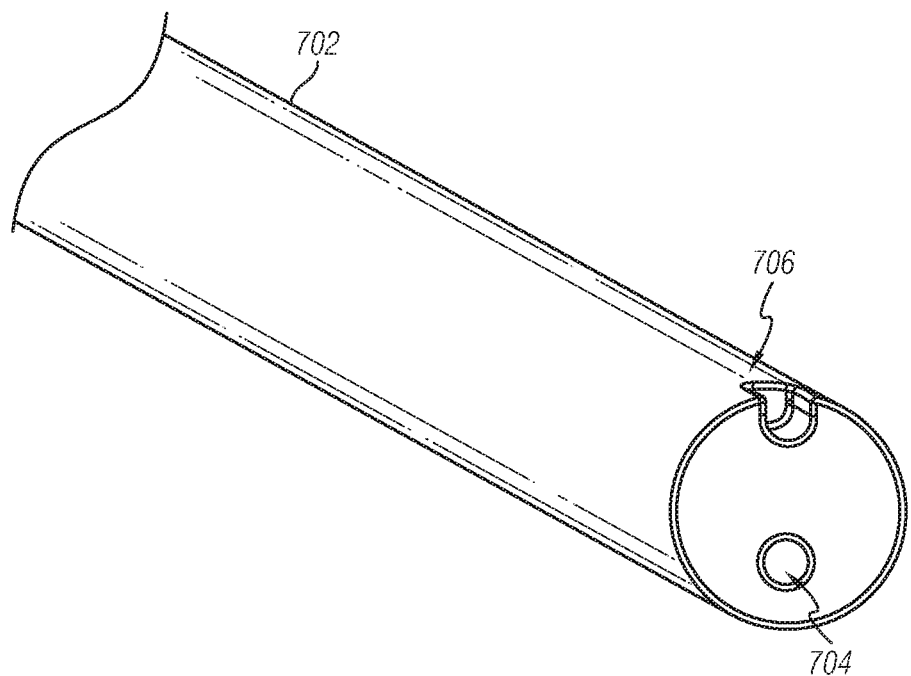
FIG. 26 illustrates a perspective detail view of a core member, according to some embodiments.

FIG. 26 illustrates an embodiment of a core member 702 according to the subject technology. The core member 702 can comprise a proximal end and an opposing distal end. In some embodiments, the cross-sectional profile of the core member 702 can be circular; however, the cross-sectional profile may comprise a polygonal shape, rounded shape, and be a regular or irregular shape. For example, the engagement member can comprise a core member coupled to the distal end portion, the core member having an outer diameter less than an outer diameter of the distal end portion. In some embodiments, the core member outer diameter can be less than about 0.030 inches, less than about 0.025 inches, or less than about 0.020 inches. In some embodiments, the core member outer diameter can be about 0.018 inches, about 0.016 inches, or about 0.014 inches.

In accordance with some embodiments, the core member 702 may include a lumen 704 extending between the proximal and distal ends. The lumen 704 can be configured to receive the release component there within, which in some embodiments can comprise an elongate wire.

Optionally, the core member 702 can comprise a slot for engaging a free end of the release component to facilitate or retain the release component in the engaged position. For example, as illustrated in FIG. 26, the core member 702 can comprise a slot 706 that extends through an outer surface of the distal end portion. The slot 706 can extend proximally from the distal end of the core member 702 along an outer surface thereof. In another embodiment, the slot 706 extends proximally through the outer surface of the distal end and side of the core member 702. The slot can comprise a cross-sectional profile that is larger than a cross-sectional profile of the distal end portion of the release component. However, the slot can also have a cross-sectional profile that is less than a corresponding cross-sectional profile of the distal end portion of the release component in order to provide a frictional engagement or interference fit that can be overcome through manual actuation, releasing of a bond (e.g., electrolytic detachment, a chemical reaction, or dissolution of a bonding agent upon exposure to the body lumen), or by the force of the biasing or self-expansion of the release component.

Figure 27:
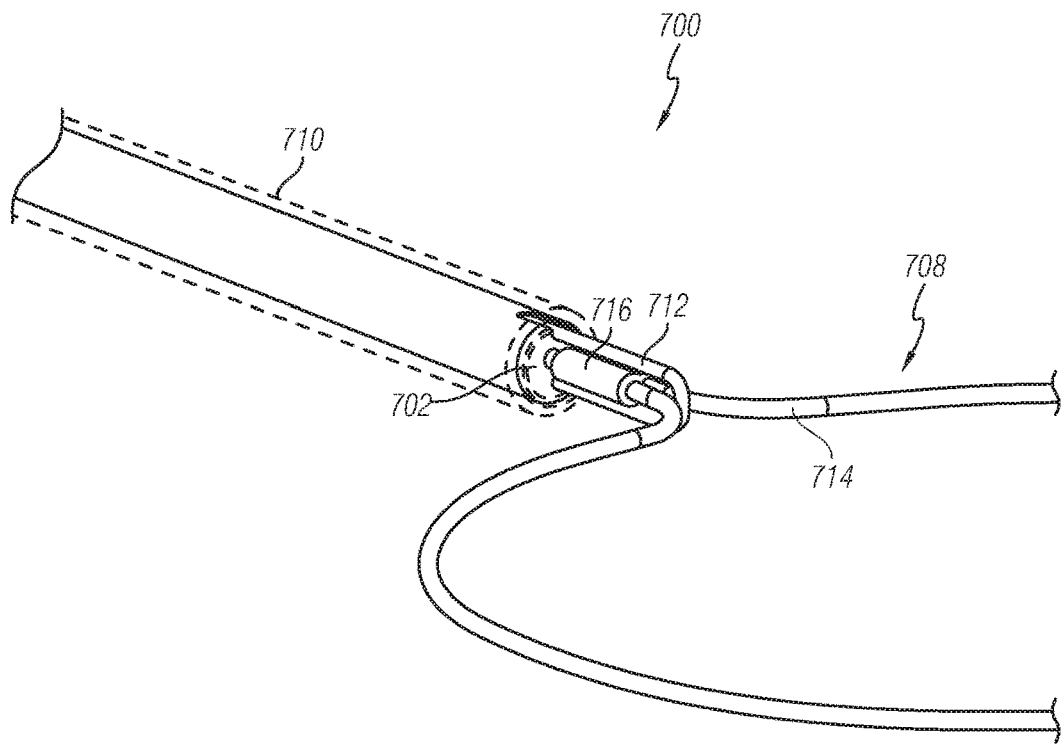
FIGS. 27-29 illustrate a perspective detail views of an implant carrier assembly, according to some embodiments.
Figure 28:
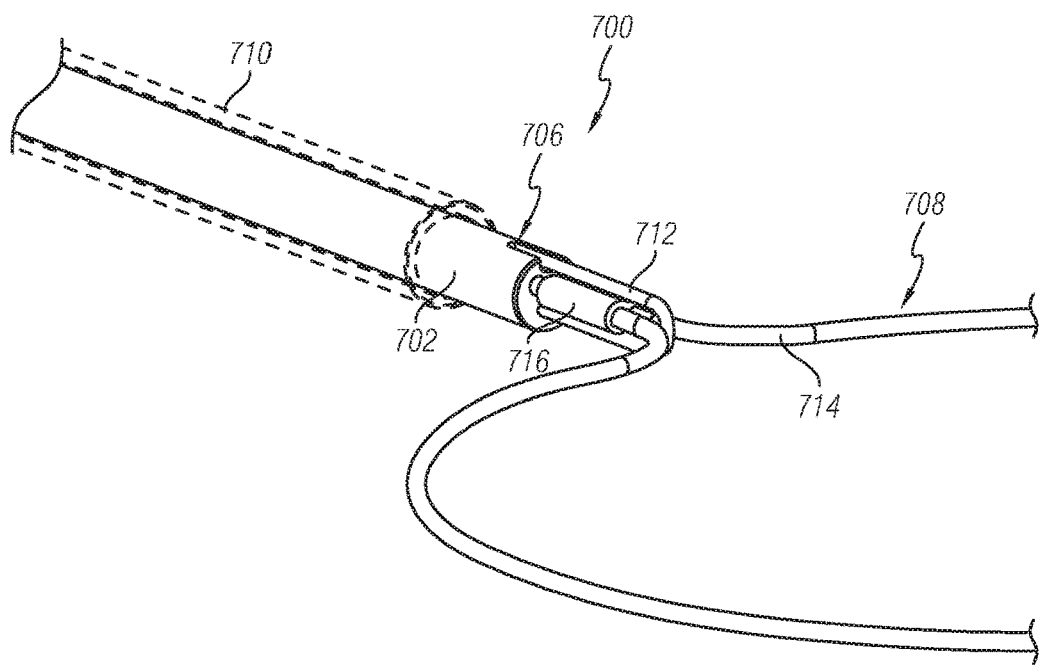
Figure 29:
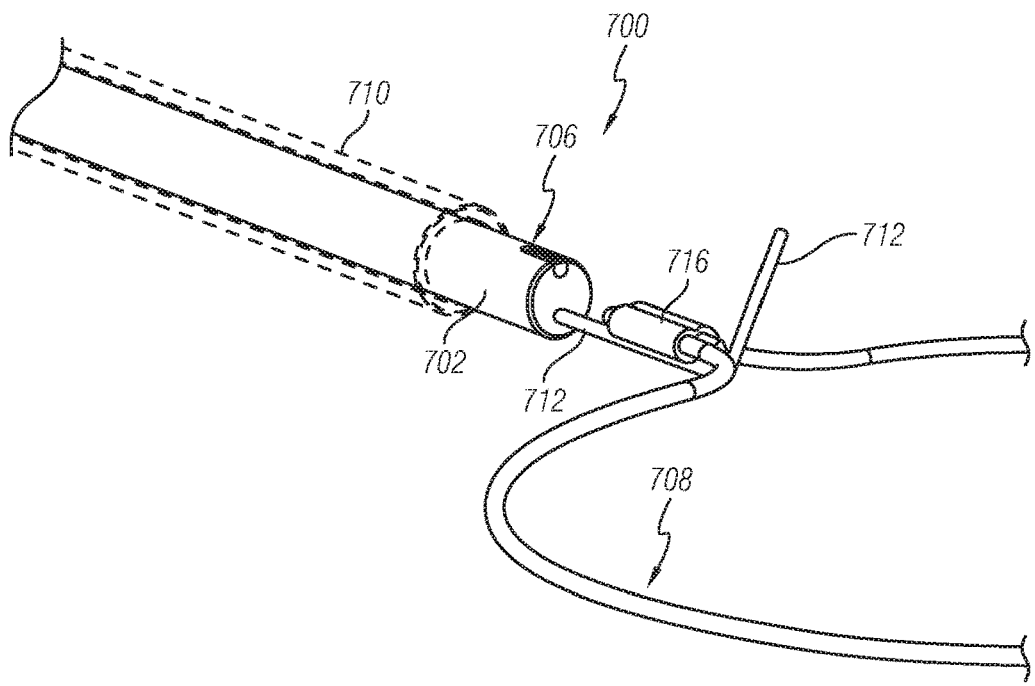

FIG. 27 illustrates a perspective view of an implant carrier assembly 700 and an occlusive implant 708. The implant carrier assembly 700 can comprise a sheath 710 having a proximal end and an opposing distal end, a lumen, and an inner surface. The sheath 710 can be configured such that the core member 702 extends within the lumen, and is moveable between the proximal and distal ends of the sheath 710. For example, the sheath can extend within a lumen of a catheter. In some embodiments, the catheter can have an outer diameter of less than about 0.050 inches, less than about 0.045 inches, less than about 0.040 inches, or about 0.036 inches.

At the distal end portion of the core member 702, a release wire 712 can be configured to engage the occlusive implant 708. The release wire 712 can be operably coupled to or positioned at the distal end portion of the core member 702. For example, the release wire 712 can comprise an elongate wire that can extend within a lumen 704 of the core member 702. The release wire 712 can comprise a distal portion extending out of the core member lumen 704 beyond the core member distal end. In some embodiments, the distal portion of the release wire 702 can comprise a hook or deflectable segment that can move between engaged and disengaged positions. The release wire 702 can comprise a deflectable, resilient, elastic, shape memory, and/or biased component or material. Further, in some embodiments, the release wire 702 can maintain a generally hook-shaped, looped, or bent configuration in engaged and disengaged positions. Alternatively, the release wire 702 can move from a hook-shaped, looped, or bent configuration to a substantially straight or less-bent configuration when moving from the engaged position to the disengaged position.

In accordance with some embodiments, in the engaged position, as illustrated in FIG. 27, the core member 702 can be disposed within the sheath 710 such that the distal end of the core member 702 is proximally aligned with the distal end of the sheath 710. The distal end portion of the core member 702 can be positioned proximal to the distal end of the sheath 710 in the engaged position. In the engaged position, the distal portion of the release wire 712 can extend distal to the distal end of the core member 702 and reverse to create a loop. In accordance with some embodiments, in the engaged position, the release wire 712 can loop around or engage with a portion of the implant 708 and at least a section or terminal end portion of the release wire 712 can be positioned within the sheath 710 or captured between the sheath 710 and the core member 702 to secure the section or terminal end portion of the release wire 712 relative to the core member 702 in the engaged position. For example, the core member 702 can comprise a slot 706 that can be configured to receive the distal end of the release wire 712. In some embodiments, the distal end of the release wire 712 can be interposed between the core member 702 and the inner surface of the sheath 710. In an aspect, the distal end of the release wire 712 contacts or engages the slot 706 and the inner surface of the sheath 710 in the engaged position.

In the engaged position, the occlusive implant 708 can be retained by the implant carrier assembly 700. For example, a proximal portion of the occlusive implant frame 714 may include an implant proximal coupling member 716 or otherwise be joined or welded in a proximal segment thereof. In any of such embodiments, first and second wires of the occlusive implant 708 can thereby converge and be joined, for example, by welding or otherwise extending through the implant proximal coupling member 716, if used. To retain the occlusive implant 708, the distal portion of the release wire 712 can extend through the lumen 704, loop around the implant (e.g., through the proximal ring or hoop of the implant, around proximal coupling member 716, or around/into a slot or hook on the proximal coupling member 716), and terminates in the slot 706. The loop of the release wire 712 can constrain longitudinal movement of the implant 708 relative to the core member 702. In some embodiments, the release wire 712 can extend through a first lumen of the core member 702, loop around the implant proximal coupling member 716, and extend through a second lumen of the core member 702.

In some embodiments, the distal portion of the release wire 712 comprises a length of at least about twice as long as a longitudinal length of the implant proximal coupling member 716. The distal portion of the release wire 712 may comprise a length of at least about 2.5 times as long as a length of the implant proximal coupling member 716.

Once in the engaged position, the assembly 700 can be advanced through an introducer catheter toward the target site within the body lumen. Thereafter, referring to FIG. 28, to release the occlusive implant 708 from the implant carrier assembly 700, the core member 702 can be moved relative to the sheath 710 until a distal portion of the core member 702 is positioned distally beyond the distal end of the sheath 710. In some embodiments, the core member 702 can be advanced distally within the sheath 710 such that the slot 706 is positioned distally beyond the distal end of the sheath 710.

Accordingly, the implant carrier assembly 700 may be actuated or moved to the released position when the core member distal end is positioned distally beyond the sheath distal end. In the released position, illustrated in FIG. 29, the release wire distal portion can be resiliently biased away from the core member slot 706. The release wire 712 may be configured to automatically bias away from the core member slot 706. For example, the release wire distal portion may be resiliently biased to a substantially straight configuration when the implant carrier assembly 700 is in the release position. In some embodiments, the distal portion of the release wire 712 is positioned outside of the core member slot 706. For example, the release wire 712 may comprise a shape memory alloy, e.g., nickel titanium, such that the release wire 712 is directed into a rigid configuration in the engaged position, and into a relaxed configuration in the released position. In some examples, the release wire 712 may be in a relaxed configuration in the engaged position, and directed into a rigid configuration in the released position such that the wire forms a substantially straight configuration. This movement of the release wire 712 can result in disengagement or loosening of the engagement between the assembly 700 and the implant 708.

However, in some embodiments, the release wire can also or instead be configured to be actuated or moved into the released position while the distal end of the core member 702 is positioned within the lumen of the sheath 710. For example, the core member 702 may include a release mechanism associated with the distal end of the release wire 712, such as an electrolytic detachment or dissolvable bond that can be actuated by the clinician or actuated after a certain period of time in the presence of body fluid, thereby permitting the wire to be released and the core member 702 directed away from the occlusive implant 708. In another example, a release wire 712 can comprise a shape memory material that may be actuated by the clinician to engage or release the occlusive implant 708 by proximally retracting the wire within the lumen. Further, some embodiments can optionally omit the use of the sheath 710 and rely solely on manual actuation and disengagement of the wire 712 by the clinician.

Figure 30:
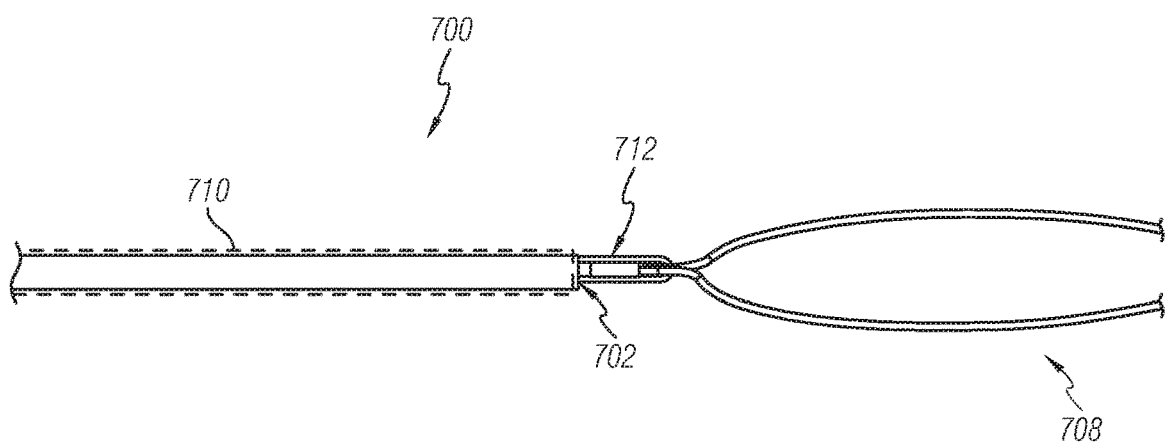
FIGS. 30-32 illustrate side section views of an implant carrier assembly, according to some embodiments.
Figure 31:
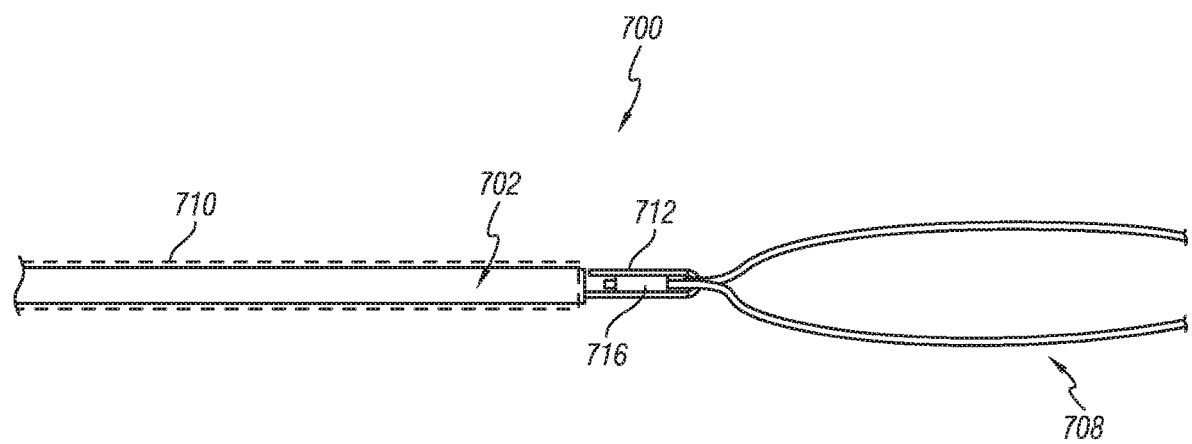
Figure 32:
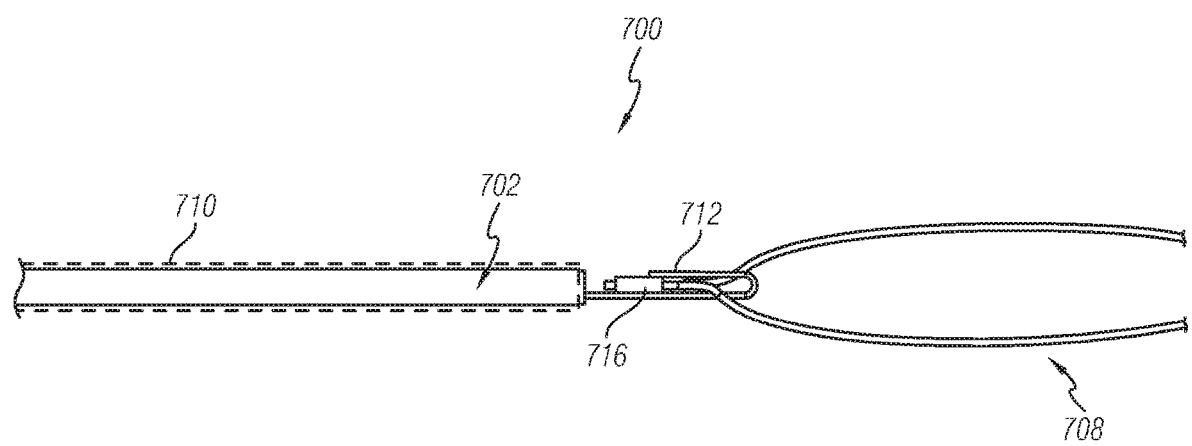

For example, in some embodiments, referring to FIGS. 30-32, the implant carrier assembly 700 may be configured to release the occlusive implant 708 by directing the distal portion of the release wire 712 distally from the distal end of the core member 702 and sheath 710 (which can instead be an introducer catheter in embodiments in which the sheath 710 is omitted). In this configuration, the clinician can maintain the relative longitudinal positions of the core member 702 and the sheath 710 while the release wire 712 is moved distally relative to the assembly 700. Referring to FIG. 31, in some embodiments, the release wire 712 can remain engaged around the implant proximal coupling member 716 (e.g., the wire can be configured without the properties of self-biasing or self-straightening from a hook-shaped or bent configuration), the occlusive implant 708 can be directed distally with the release wire 712 until the wire 712 is disengaged from the implant 708. With the occlusive implant 708 positioned in the lumen in an expanded configuration, the release wire 712 can be moved distally beyond the implant proximal coupling member 716, for example, as illustrated in FIG. 32. Upon moving distally to the implant proximal coupling member 716, the release wire 712 can be retracted from the occlusive implant 708.

Figure 33:
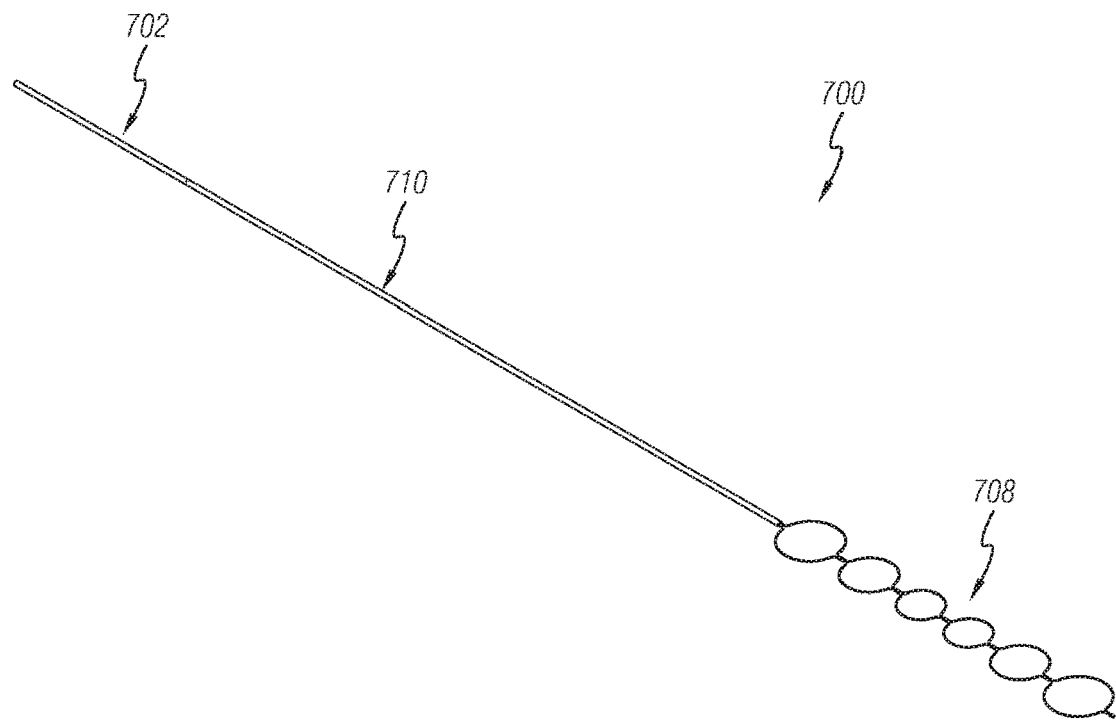
FIG. 33 illustrates a perspective view of an implant carrier assembly, according to some embodiments.

FIG. 33 illustrates the occlusive implant 708 in an expanded configuration with the occlusive implant 708 and the implant carrier assembly 700 in an engaged position. In the engaged position, the core member 702 extends through a lumen of the sheath 710, while a distal end of the core member 702 can be coupled to a proximal portion of the occlusive implant 708. While engaged, the sheath 710 can be proximally advanced relative to the implant 708 in order to collapse the implant profile and move the implant 7082 a collapsed configuration within the sheath 708, in preparation for delivery to the target site.

FIGS. 34-42 illustrate additional embodiments of an implant carrier assembly and implant attached thereto. The carrier assembly 800 can be removably coupled to an occlusive implant 802. In some embodiments, the implant carrier assembly can comprise a pusher member and one or more engagement arms that extend through a sheath. The implant carrier assembly 800 can be configured to engage and retain an occlusive implant in an engaged position, and to release an occlusive implant in a disengaged position.

Figure 34:
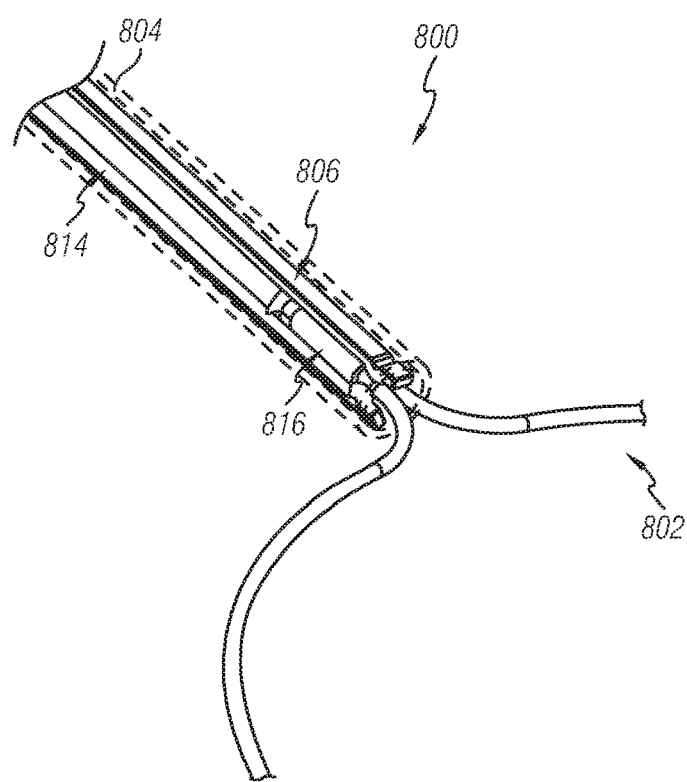
FIG. 34 illustrates a perspective detail view of an implant carrier assembly, according to some embodiments.

Referring to FIG. 34, the sheath 804 can comprise a proximal end and an opposing distal end, a lumen, and an inner surface. The assembly 800 can comprise an engagement mechanism 806 having a base 808 and one or more engagement arms 810. The engagement arm(s) 810 can have a proximal end and an opposing distal end. In some embodiments, the engagement arms 810 can comprise a base at the proximal end such that the arms extend distal to the base 808. The engagement arms 810 of the engagement mechanism 806 can extend through the lumen of the sheath 804, and can be configured to move proximal to or distal to the distal end of the sheath 804.

Figure 38:
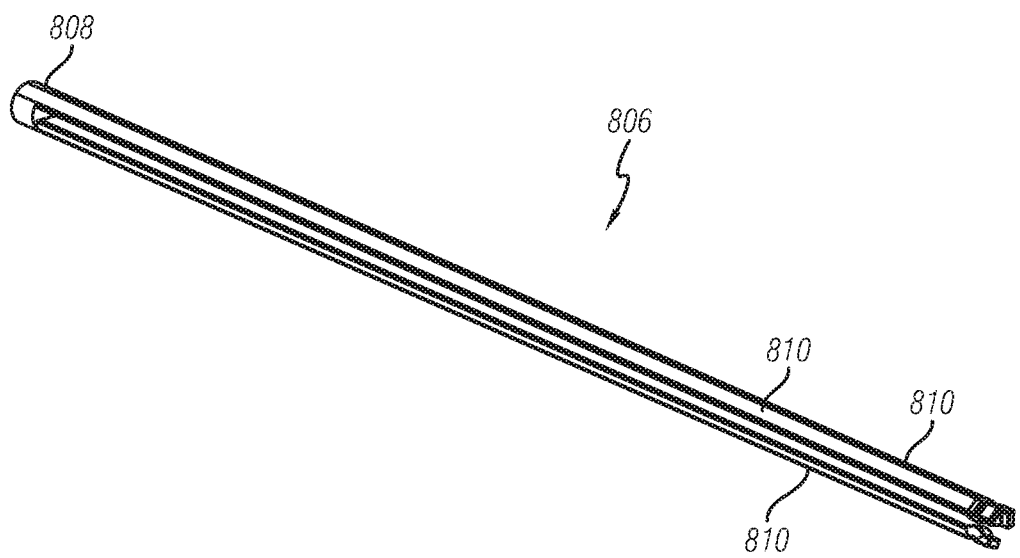
FIG. 38 illustrates a perspective view of a plurality of engagement arms, according to some embodiments.

Referring to FIG. 38, in some embodiments, the engagement mechanism 806 can comprise a base 808 that is operably coupled to the arms 810. The base 808 can be shaped as a cylinder and can comprise a passage therethrough. The arms 810 extend from the distal end of the base such that a passage extends along a longitudinal axis between the proximal and distal ends of the engagement arms 810.

Figure 39:
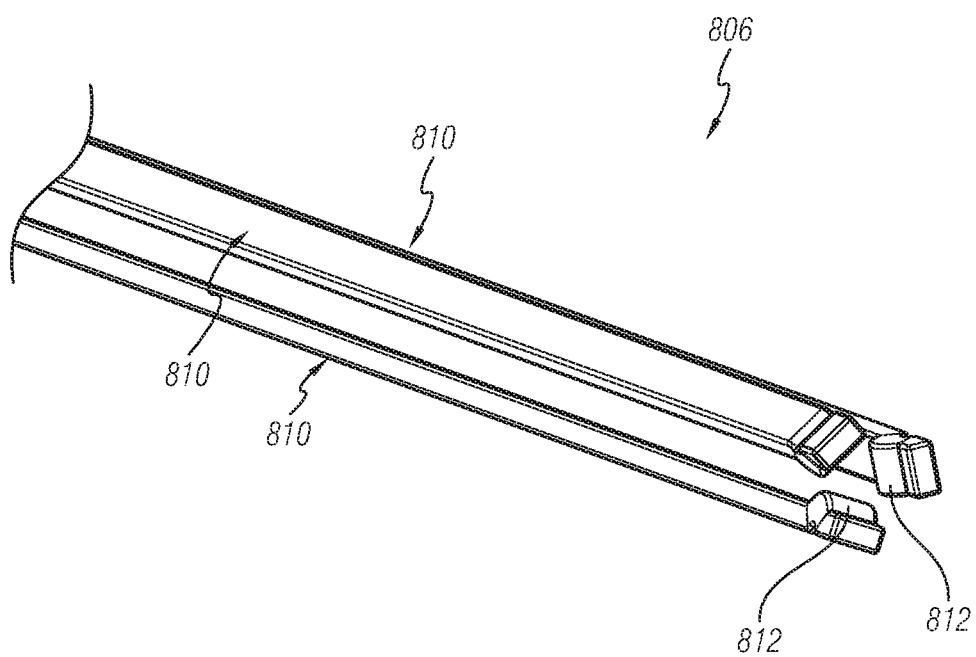
FIGS. 39-42 illustrate a perspective detail views of the engagement arms, according to some embodiments.
Figure 40:
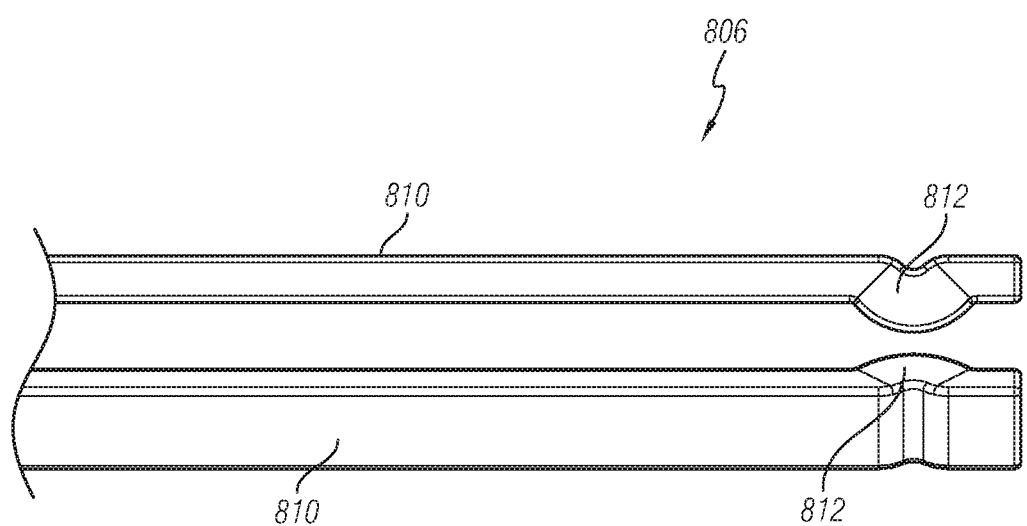
Figure 41:
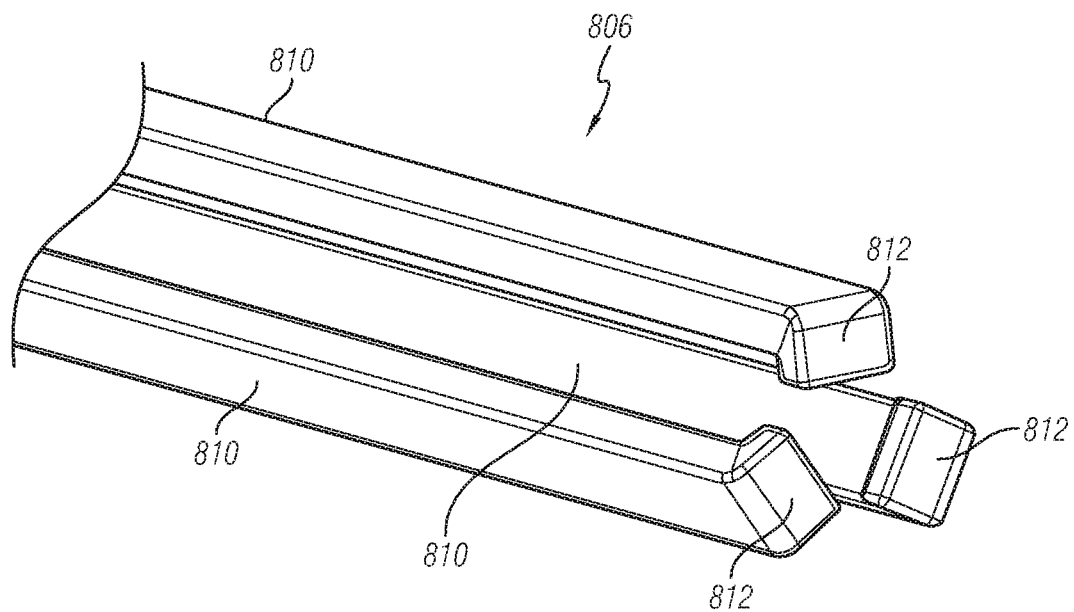
Figure 42:
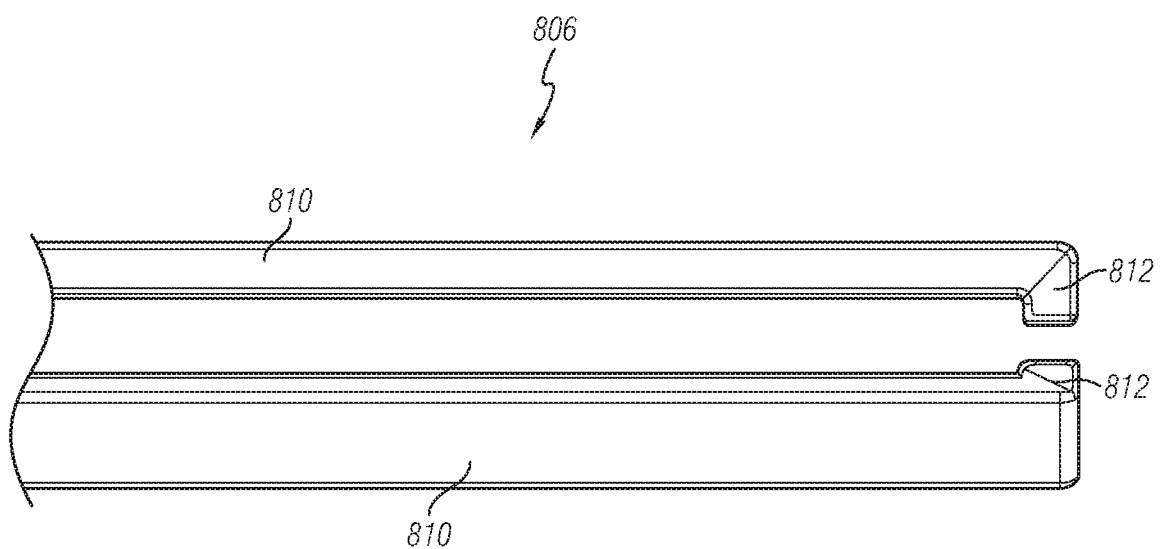
Figure 43:
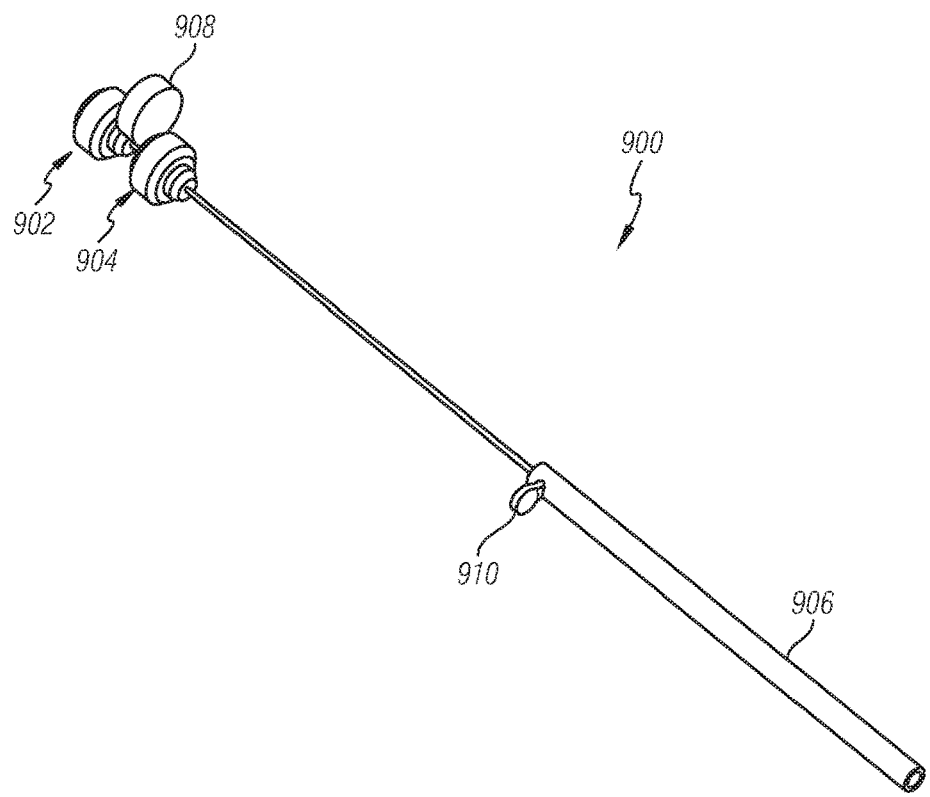
FIG. 43 illustrates a perspective view of an implant carrier assembly, according to some embodiments.

Each of the arms 810 can comprise a protrusion 812 extending radially inwardly. Referring to FIGS. 39-40, a protrusion 812 may be positioned proximal to the distal end of each arm 810. In accordance with some embodiments, an inner surface of each protrusion 812 may be shaped as a triangular, convex, or arcuate surface or structure. In some embodiments, the outer surface of each arm 810 may have a concave surface longitudinally aligned with the convex surface. Referring to FIGS. 41 and 42, a protrusion 812 may be positioned at a distal end of the arm 810. Each protrusion 812 may extend radially inward from the distal end of each arm 810. In some embodiments, the engagement arms 810 can comprise at least two arms, but can include three, four, five, or more arms 810. In some embodiments, three arms 810 can be circumferentially spaced apart from each other.

Referring to FIGS. 34-37, the implant carrier assembly 800 can comprise a pusher 814 having a proximal end and an opposing distal end. The pusher 814 can comprise a cross-sectional outer profile along a longitudinal axis between the proximal and distal ends. The outer cross-sectional profile can correspond to a cross-sectional complementary or inner profile defined by one or more of arms 810, for example, through a central passage defined between the engagement arms 810 (as shown in FIGS. 34-37). However, the pusher 814 can be paired with a single arm 810. Further, the pusher 814 and the arm or arms 810 can be formed from separate components or formed as a unitary component or from a single, continuous piece of material.

In some embodiments, the outer surface of the pusher 814 can be configured to engage an inner surface of the passage through the base 808 of the engagement arms 810 and between the arms 810. The pusher 814 can be configured to extend through the passage of the engagement arms 810. In some embodiments, a length of the pusher 814 between the proximal and distal ends is less than a length between the proximal end and the protrusion 812 of each arm 810. Further, the pusher 814 can be longitudinally movable relative to the arms 810 in order to be advanced distally relative to the arms 810 to push an implant coupling member 816 distally beyond the arms 810. For example, in embodiments in which the arms 810 are not resiliently biased to an open or expanded state after being pushed distally beyond the distal end of the sheath 804, the pusher 814 can be actuated by the clinician to distally advance the implant coupling member 816 distally beyond the arms and protrusions thereof in order to disengage the implant coupling member 816 therefrom.

Figure 35:
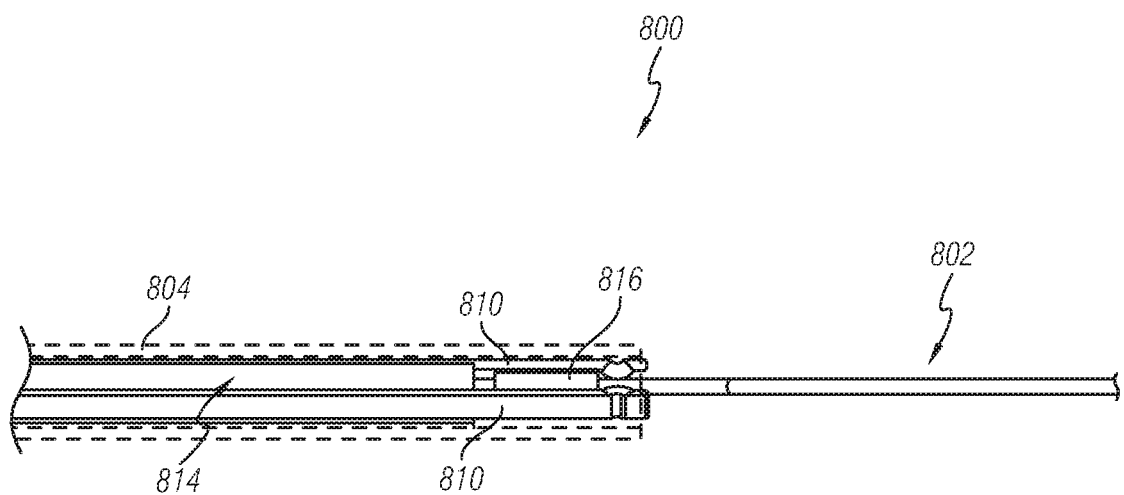
FIGS. 35-37 illustrate section views of an implant carrier assembly, according to some embodiments.
Figure 36:
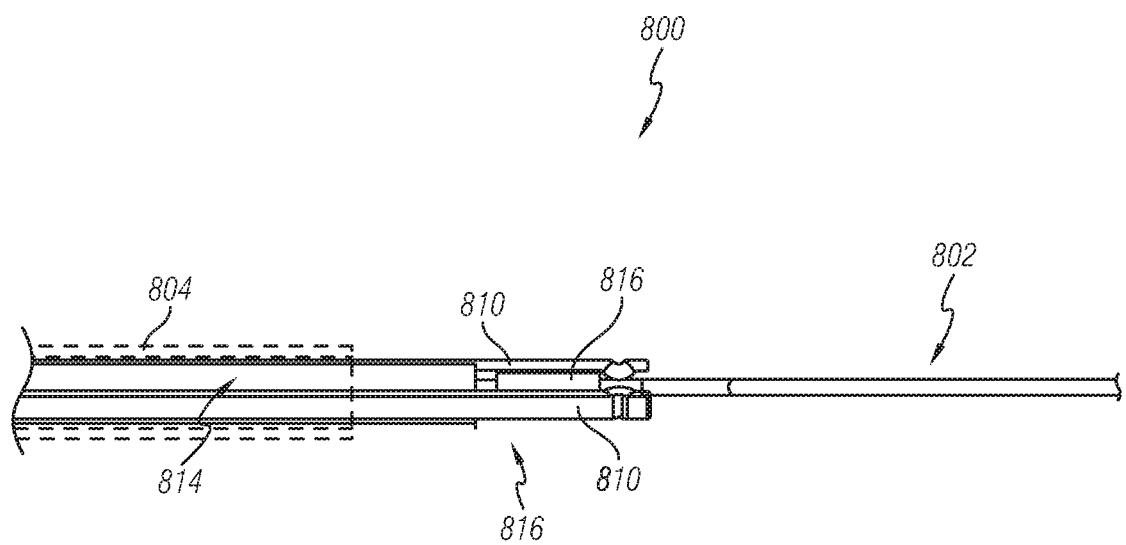

In an engaged position, illustrated in FIGS. 34 and 35, the engagement arms 810 can be disposed within the sheath 804 such that the distal end of the arms 810 are proximally aligned with the distal end of the sheath 804. This positioning can maintain the arms 810 collapsed around the implant coupling member 816. In some embodiments, the distal end of the arms 810 and can be positioned proximal to the distal end of the sheath 804 in the engaged position. However, the arms 810 can also extend no further than a position in which the engagement region of the arms 810 (the pocket in which the implant coupling member 816 is disposed) is positioned distally beyond the distal end of the sheath 804. A distal portion of the engagement arms 810 can be configured to retain a proximal portion of the occlusive implant 802 (e.g., to maintain the implant coupling member 816 in the engagement region). For example, a proximal portion of the occlusive implant frame may include the implant proximal coupling member 816 or other such structure that can be engaged or whose motion can be limited by one or more arms 810. In an engaged position, the implant proximal coupling member 816 can be positioned between the arms 810 proximal to the protrusions 812. This location, as illustrated in FIG. 36, can be referred to as the engagement region. In this position, the outer surface of the implant proximal coupling number 816 may be engaged against an inner surface of one or more the arms 810 or against an inner surface of an arm and an inner surface of the sheath 804. In accordance with some embodiments, a distal end of the pusher 814 can be configured to push the occlusive implant 802 distally beyond the arms 810 in order to initiate release of the implant.

Referring to FIG. 36, in accordance with some embodiments, to release the occlusive implant 802 from the implant carrier assembly 800, the engagement arms 810 and the pusher 814 can be directed through the sheath 804 until a distal portion of the arms 810 is positioned distally beyond the distal end of the sheath 804. The occlusive implant 802 may be disengaged from the implant carrier assembly 800 by pushing the implant proximal coupling number 816 using the pusher 814.

Alternatively, or in addition to some embodiments comprising a pusher that is distally movable relative to one or more arms, the engagement mechanism 806 can comprise one or more arms 810 that can be biased to radially separate from the longitudinal axis of the sheath or separate from each other when the arm(s) is positioned distal to the distal end of the sheath 804. For example, some embodiments can be configured such that the arm(s) and the pusher are formed as a unitary component or from a single, continuous piece of material, and the arm(s) can be biased or spring away from the longitudinal axis of the sheath. Thus, when the engagement mechanism 806 moves beyond a distal end of the sheath 804, the engagement mechanism 806 can automatically release the implant therefrom.

For example, the arm(s) 810 can comprise a shape memory material that can be activated to cause the arm(s) to move from one position to another (e.g., an alloy or polymer that can be activated by temperature, electricity, light, chemical, or otherwise). When the shape memory material is activated, the arms 810 bias radially outward, away from each other, thereby permitting the occlusive implant 802 to be released. In some embodiments, the shape memory material can maintain the arm(s) 810 in a radially collapsed configuration, wherein the implant proximal coupling number 816 is engaged by the engagement arms 810 until the shape memory is activated and causes the arm(s) 810 to separate from the longitudinal axis or other arms, thus opening the engagement region and allowing the proximal coupling member 816 to be separated therefrom.

Figure 37:
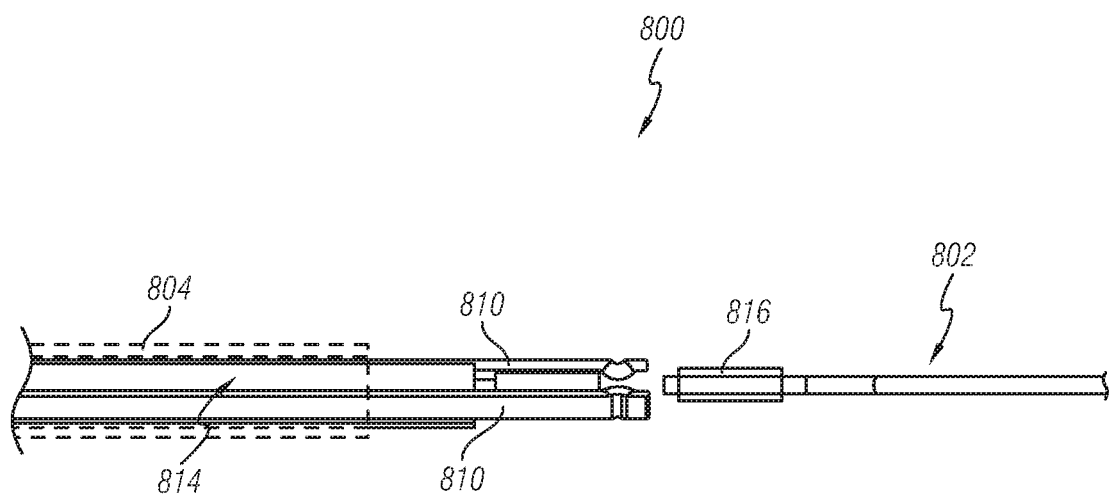

Optionally, in some embodiments, the pusher 814 can be distally advanceable within the sheath 804 lumen to move the engagement arm(s) 810 from the engaged position to the disengaged position, as illustrated in FIG. 37. For example, whether or not the arm(s) 810 are biased to an open or expanded state, the pusher 814 can be used to urge the implant proximal coupling number 816 away from the engagement arms 810 and/or out of the engagement region.

The implant carrier assembly, in some embodiments, can comprise a handle assembly. The handle assembly can comprise at least one slidable member to actuate the engagement mechanism of the assembly. For example, the slidable member can be coupled to the pusher/engagement arm(s) to controlled distal advancement of the pusher/engagement arm(s) relative to the sheath. The assembly can also be configured to comprise two slidable members, one being operably connected to the pusher/engagement arm(s) and the other being operably connected to the sheath. The assembly can also be configured to comprise two slidable members, one being operably connected to the pusher and the other being operably connected to the engagement arm(s). Moreover, the assembly can also be configured to comprise three slidable members, one being operably connected to the pusher, one being operably connected to the engagement arm(s), and the other being operably connected to the sheath. Other variations and configurations can be performed within the scope of the disclosure presented herein. These slidable members can be coupled to each other and/or to the guide catheter or sheath in order to maintain a fixed relative positioning thereof, as discussed with respect to some embodiments herein.

In accordance with some embodiments, FIGS. 43-47 illustrate an assembly 900 that comprises a first slidable member 902 and a second slidable member 904. The first slidable member can be coupled to a proximal end of the pusher 814, and the second slidable member can be coupled to a proximal end of the engagement arm(s) 810. The first and second slidable members can have a first configuration in which the first and second slidable members are coupled together. In the first configuration, the first and second slidable members can move in unison together as a single unit. For example, the first and second slidable members may be advanced through the sheath 804 such that a portion of the engagement arms 810 and the pusher 814 extend distal to the distal end of the sheath 804, as illustrated in FIG. 36. Because of their fixed relative positioning in the first configuration, the stent can remain engaged with the assembly during movement of the first and second slidable members. In a second configuration of the first and second slidable members, the first and second slidable members can be movable relative to each other, for example, to effectuate releasing of the stent. In the second configuration, the pusher 814 can be permitted to move relative to the engagement arms 810. For example, the first slidable member may be advanced to push or advance the occlusive implant 802 distally through the engagement arms 810.

Referring to FIGS. 43-47, the handle assembly 900 can comprise a first slidable member 902 and a second slidable member 904. The first slidable member 902 can comprise a proximal end, an opposing distal, and a lumen extending between the proximal and distal ends. The second slidable member 902 can be configured to be advanced through a catheter 906 such as those described in the present disclosure. The first slidable member 904 can comprise a proximal end and a distal end. The first slidable member 904 can be configured to be advanced through the lumen of the second slidable number 902. In some configurations, with the first slidable member 904 extended within the lumen of the second slidable member 902, a spacer pin 908 can be interposed between the first and second slidable members. In some embodiments, a locking pin 910 can couple the first or second slidable members to each other and/or to the catheter.

Figure 44:
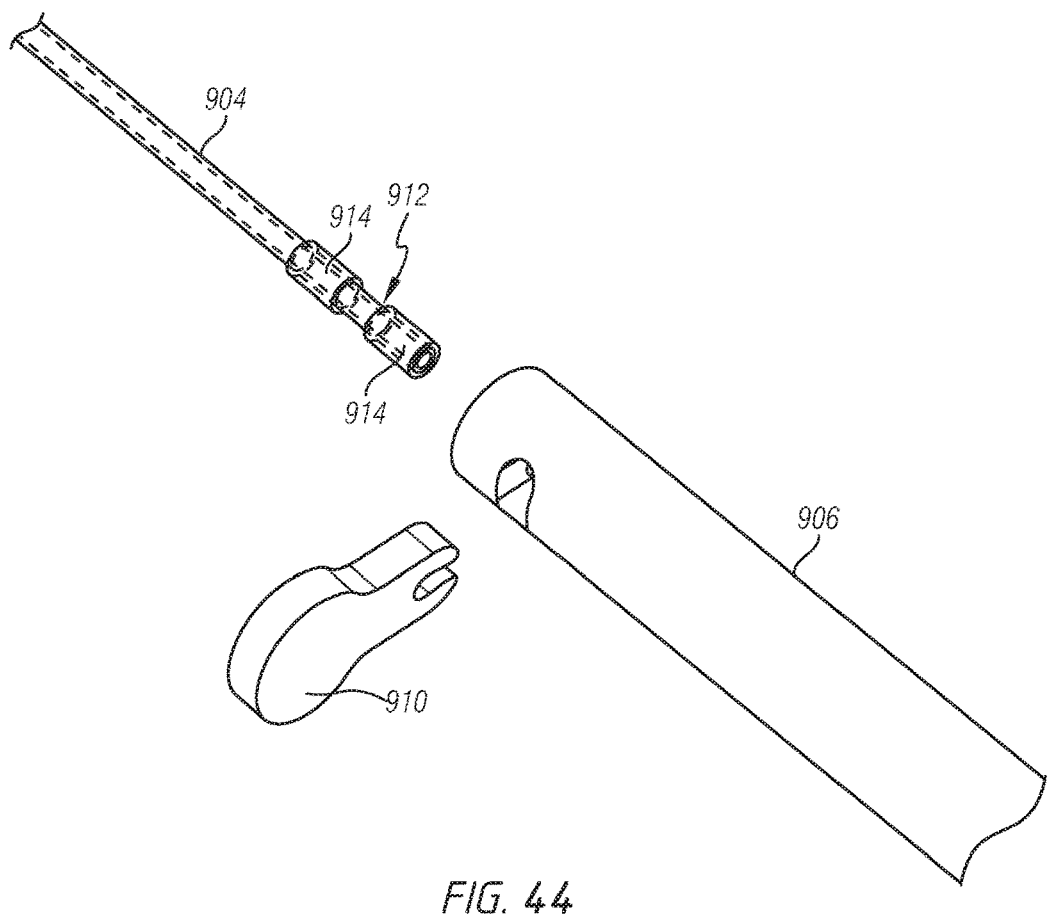
FIGS. 44-47 illustrate a perspective detail views of the engagement arms, according to some embodiments.
Figure 45:
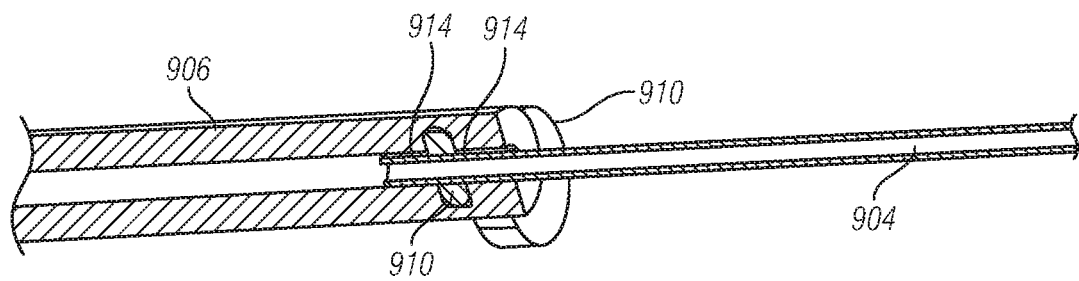

Referring to FIG. 44, the second slidable member 904 (which can be the sole slidable member in embodiments that use only one slidable member) can comprise at least one groove 912 around the circumference of an outer surface of the second slidable member. For example, the slidable member can comprise a groove positioned proximal to the distal end and/or one or more grooves positioned at other locations along the length of the slidable member. In some embodiments, the groove can be formed by a pair of adjacent hypotubes or circumferential rings 914 that extend from a distal portion of the outer surface of the second slidable member 904. The circumferential rings 914 can be spaced apart to form the groove 912. The groove can have a width that can be equal to or greater than the thickness of the locking pin 910. FIG. 45 illustrates a locked position in which the locking pin 910 is inserted through an aperture through a proximal portion of the catheter 906 and a pair of tangs extends across the groove 912 between the circumferential rings 914. In the locked position, longitudinal movement of the second slidable member 904 through the catheter 906 is restricted.

Figure 46:
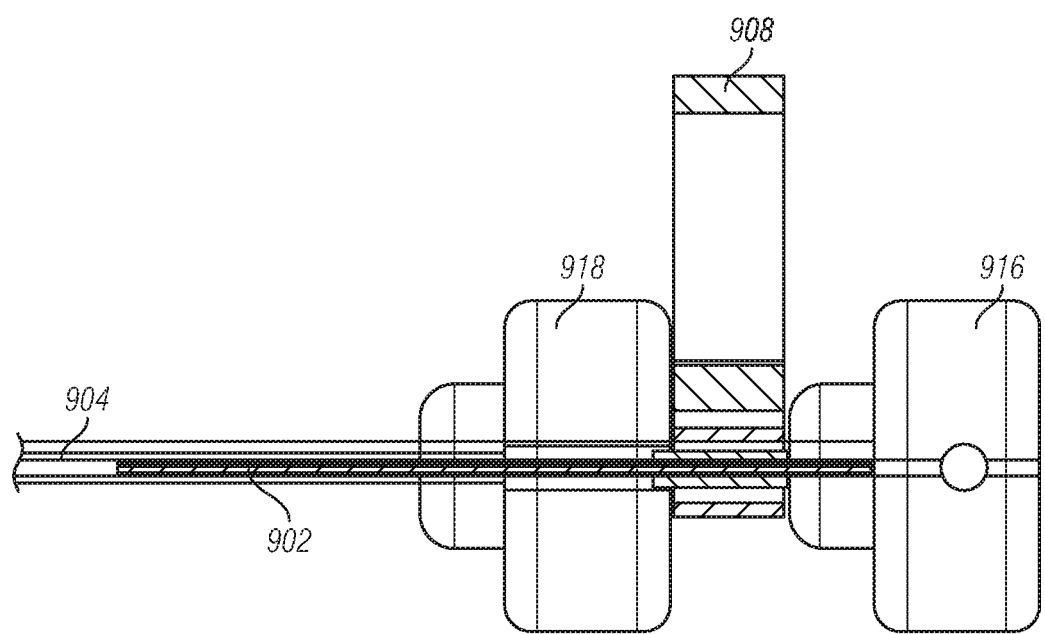
Figure 47:
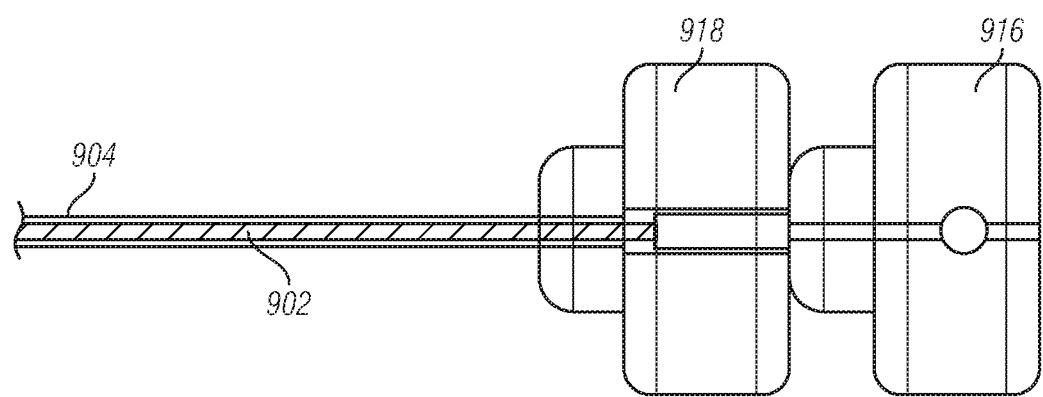

Referring to FIG. 46, the proximal end of the first slidable member 902 can comprise a first knob 916, and the second slidable member 904 can comprise a second knob 918. In some configurations, the spacer pin 908 can be coupled to the first slidable member 902, between a proximal end of the first slidable member 902 and the second slidable member 904. For example, the spacer pin 908 can be removably engageable with the proximal end of the engagement member to secure a longitudinal position of the components operably coupled to the first and second slidable members. For example, the spacer pin can limit relative movement between the pusher, the arm(s), and/or the sheath relative to each other. In particular, the spacer pin can be used to prevent release of the implant from the system. As such, when the spacer pin is present and engaged with the system, the implant can be secured with the system. Similarly, when the clinician desires to release the implant, the spacer pin can be removed in order to facilitate movement of the components of the system and release of the implant. In some embodiments, the spacer pin can be positionable between and in contact with the first and second knobs.

In some embodiments, the first slidable member 902 can be coupled to a proximal end of an engagement member, a core member, or a pusher member as described herein, and the second slidable member 904 can be coupled to a proximal end of the sheath or one or more engagement arms, as described herein.

The first and second slidable members can have a first configuration, illustrated in FIG. 46, in which the first and second slidable members can be coupled together by the spacer pin. In the first configuration, the first and second slidable members can move in unison together as a single unit. For example, the first and second slidable members may be advanced through the catheter 906 such that a portion of an engagement member and a sheath extend distal to the distal end of the catheter 906. In a second configuration, illustrated in FIG. 47, of the first and second slidable members can be movable relative to each other. Further, in the second configuration, the engagement member can be permitted to be moved relative to the sheath. For example, the second slidable member 904 may be retracted to direct the sheath proximal to a distal end of the engagement member.

For example, to insert and deploy and occlusion implant, the catheter can be advanced through a lumen, e.g., an artery, with the first and second slidable members in the locked position with the catheter. The catheter can be advanced through the lumen until the distal end of the catheter is positioned where the occlusion implant is to be placed. Next, the locking pin can be removed and the first and second slidable members can be directed together through the catheter in the first configuration such that the distal ends of the first and second slidable members approach the distal end of the catheter. The first and second slidable members can therefore advance the occlusion implant to a location at which the implant can be released from the catheter distal end into the lumen. To release the proximal portion of the occlusion implant from the implant carrier assembly, the spacer pin can be removed, and the first slidable member can be further advanced through an relative to the second slidable member, thereby directing a proximal portion of the occlusion implant through the distal portion of the second slidable member. Next, implant carrier assembly, including, for example, the first and second slidable members and the catheter, can be retracted from the lumen.

In some configurations, when the distal end of the occlusion implant begins to deploy to the expanded configuration, the first and second slidable members and the catheter can be retracted from the lumen such that the remaining portion of the occlusion implant can be deployed from the implant carrier assembly. Because the occlusion implant expands as it is release from the implant carrier assembly, the first and second slidable members and the catheter may be retracted at different rates.

Cover Component Features

As disclosed above, in some embodiments, the implant can comprise at least one cover component, membrane, mesh, or patch to assist in occluding, partially or completely, a luminal structure in which a respective implant is deployed. A cover component may be attached to one or both ends or support elements of an implant and/or to a middle region of an implant. The cover component can be configured as those disclosed in copending U.S. patent application Ser. No. 14/628,096, filed on Feb. 20, 2015 (086538-0063), the entirety of which is incorporated herein by reference.

Figure 49:
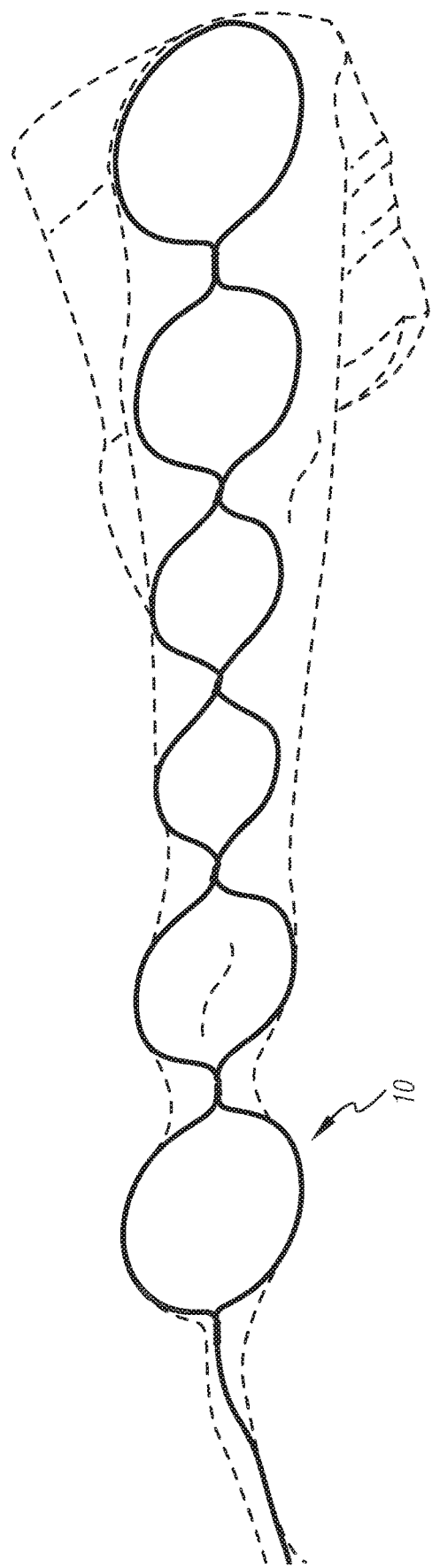
FIG. 49 illustrates a side view of an occlusive implant, according to some embodiments.

Referring to FIG. 49, in some embodiments, the cover component may be attached to each hoop structure by using an ePTFE membrane and fusing two or more layers of the ePTFE together. In some embodiments, the ePTFE membrane can be an unsintered ePTFE. In some embodiments, the two or more layers of the ePTFE can be fused together by applying heat.

In accordance with some embodiments, including any of the implant structures disclosed herein, an implant can be provided in which one or more of the hoop members comprises a cover component, such as that discussed with respect to the ePTFE. For example, hoop members at the proximal and distal ends of the implant can comprise ePTFE membranes that can facilitate blockage of flow immediately upon release of the implant.

In some embodiments, a cover component can comprise at least one of a polyurethane, a polyanhidrate, PTFE, ePTFE, silicone, and other suitable materials known to those of ordinary skill in the art. In some embodiments, cover components may be elastic. In some embodiments, cover components may be permeable or non-permeable.

Some embodiments can be configured such that the cover component can carry biocompatible medications or materials, such as hydrogels, collagens, or embolic materials. Further, the implant can comprise a cover component that extends around and/or within the support frames in a variety of ways.

The cover component can comprise a mesh material that is attached to support elements of the frame of an implant. The cover component can be formed from a tubular material that extends around and encloses the support elements, and in some embodiments, the entire frame of an implant. However, the cover component can also be adhered or coupled to the support elements by themselves. In some embodiments, the cover component can comprise a single layer of material.

Additionally, some embodiments can be configured such that when released into a body lumen, the cover component can facilitate occlusion of the lumen through the use of hydrogels, collagens, adhesives, or other coatings that disrupt or reduce flow through the lumen of the implant.

In some embodiments, an average thickness of a cover component can be between about 0.0005 inches and about 0.006 inches. In some embodiments, the average thickness of a cover component may be less than about 0.0005 inches or greater than about 0.006 inches. In certain embodiments, an average thickness of a distal portion of a cover component is greater than an average thickness of a proximal portion of a cover component. Such a configuration may ensure that more flow may be reduced at the distal portion of a cover component.

In some embodiments, the average thickness of the distal portion of a cover component is between about 0.002 inches and about 0.012 inches. In some embodiments, the average thickness of the distal portion of a cover component may be less than about 0.002 inches or greater than about 0.012 inches. In some embodiments, the average thickness of the proximal portion of a cover component is between about 0.0005 inches and about 0.006 inches. In some embodiments, the average thickness of the proximal portion of a cover component may be less than about 0.0005 inches or greater than about 0.006 inches.

Valve Mechanisms

Some embodiments of the implant frame can comprise a valve mechanism that allows a portion of the implant frame to collapse, thus restricting flow through the implant, as disclosed in copending U.S. patent application Ser. No. 14/304,868, filed on Jun. 13, 2014, the entirety of which is incorporated herein by reference. Further, in accordance with some embodiments, the valve mechanisms disclosed herein can be used in a manner suitable for deploying an embolic material to a target region, such as for cancer therapy, as disclosed in copending U.S. patent application Ser. No. 14/101,171, filed Dec. 9, 2013, the entirety of which is incorporated herein by reference.

Implant Materials and Coatings

According to some embodiments of the subject technology, the support frame of the implant may comprise at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, support frame may comprise at least one of polyethylene, polyglicolide, polylactide, c-caprolactone, polycarbonate, hydroxyalkanote, para dioxinine, polytetrafluoroethylene (PTFE), expanded polytetrafluoroethylene (ePTFE), PLA, PGA, PLLA, PDLLA, PDO, PCL, and other suitable materials known to those of ordinary skill in the art.

In some embodiments, support frame and/or occlusion membrane, may comprise a bioabsorbable material, beneficially allowing for their controlled degradation. In some embodiments, support frame and/or occlusion membrane may be formed of bioabsorbable material to have a controlled degradation anywhere between about 3 months to about 3 years depending on the desired application of support frame. In some embodiments, the controlled degradation may be less than about 3 months or greater than about 3 years. For example, hydrolysis of ester linkages or effects of enzymatic degradation may be utilized for the controlled degradation.

In some embodiments, components of the implants disclosed herein, including the frame, cover component, and/or occlusive components and/or materials, may be surface finished and/or coated with various suitable agents, such as hydrogels, collagens, drugs, adhesives, and the like, to facilitate expansion of the implant, facilitate engagement of the implant within the body lumen, and/or promote occlusion by the implant of the body lumen. For example, the support frame can be coated with a material to facilitate expansion within and engagement between the implant and the inner surface of the vessel or lumen. Further, the frame, cover component, and/or occlusive components and/or materials may be coated with biological glue, hydrogels, collagens, drugs, and/or adhesive materials. In some embodiments, support frame may be coated with a friction-resistant coating (e.g., a friction-resistant polymer coating). In some embodiments, radio-opaque markers may be located on support frame or occlusion membrane for endovascular or other image-guided procedures. In some embodiments, the radio-opaque marker may be a platinum iridium alloy or other suitable markers known to those of ordinary skill in the art.

Medical Applications and Procedures for Some Embodiments

The occlusive implants, catheters, systems, and methods can be used in a variety of clinical applications, such as rapid, well-controlled, and reliable temporary or permanent vessel occlusion, stenting, or other functions in luminal structures of a patient. According to some embodiments, the implants, catheters, systems, and methods disclosed herein can be used for percutaneous, peripheral occlusion of the arterial and venous vasculature. However, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. In some embodiments, the implants, catheters, systems, and methods disclosed herein may be used for temporary occlusion in cases of lung disease, or for temporary occlusion of female reproductive organs for contraceptive purposes. In some embodiments, the implant(s) may be removed, or flow may be restored through the luminal structure to restore original organ functions.

Some embodiments of the occlusive implants, catheters, systems, and methods can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, or close an abnormal blood vessel or blood vessels supplying a vascular anomaly such as arteriovenous malformations or arteriovenous fistulas, and other conditions.

Further, some embodiments may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). Some embodiments may be used for stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). Some embodiments may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, and other such issues), and devascularization prior to (or as an alternative to) surgical resection of various organs or tumors.

Furthermore, some embodiments may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of uretero-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of the implants, catheters, systems, and methods disclosed herein is not limited to applications for human patients, but may also include veterinary applications.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

Clause 1. An expandable device for delivery to a target location in a body lumen, the device comprising: first and second elongate wires extending along a longitudinal axis and being twisted helically about each other at a plurality of positions along the axis to interconnect the first and second wires and longitudinally secure the first and second wires relative to each other, wherein the first and second wires form a hoop structure between each pair of adjacent positions, each hoop structure having an expanded configuration in which the first and second wires are resiliently spaced apart from each other and a collapsed configuration in which the first and second wires extend adjacent to or abut each other.

Clause 2. The device of Clause 1, wherein the first and second wires form at least four hoop structures.

Clause 3. The device of Clause 2, wherein the first and second wires form six hoop structures.

Clause 4. The device of any of the preceding Clauses, wherein each hoop structure has a rounded shape in the expanded configuration.

Clause 5. The device of any of the preceding Clauses, wherein each hoop structure has a circular shape in the expanded configuration.

Clause 6. The device of any of the preceding Clauses, wherein in the collapsed configuration, adjacent hoop structures extend in a substantially linear configuration along the longitudinal axis, and wherein in the expanded configuration, the adjacent hoop structures extend transverse relative to the longitudinal axis.

Clause 7. The device of any of the preceding Clauses, further comprising a cover member coupled to the device.

Clause 8. An expandable device for occluding a body vessel, the device comprising: a first closed loop, the first closed loop comprising first and second wires coupled to each other at a first location, the first and second wires diverging from the first location and converging toward each other at a second location to form the first closed loop; a helical section adjacent to the first closed loop, the first wire extending helically from the closed loop in a first direction and the second wire extending helically from the closed loop in a second direction, opposite the first direction, thereby forming the helical section; and a second closed loop, opposite the first closed loop. with the helical section disposed therebetween, the second closed loop comprising the first and second wires coupled to each other at a third location adjacent to the helical section, the first and second wires diverging from the third location and converging toward each other at a fourth location to form the second closed loop.

Clause 9. The expandable device of Clause 8, wherein the first and second wires each complete two helical revolutions in the helical section.

Clause 10. The expandable device of any of Clauses 8 or 9, further comprising a third closed loop, the first closed loop being interposed between the third closed loop and the helical section, the first and second wires coupled to each other at a fifth location and diverging from the fifth location and converging towards the first location to form the third closed loop.

Clause 11. The expandable device of any of Clauses 8-10, further comprising a fourth closed loop, the second closed loop being interposed between the fourth closed loop and the helical section, the first and second wires diverging from the third location and converging toward each other at a sixth location to form the fourth closed loop.

Clause 12. The expandable device of any of Clauses 8-11, wherein the expandable device comprises a substantially cylindrical expanded profile.

Clause 13. The expandable device of any of Clauses 8-12, further comprising a cover member coupled to the device.

Clause 14. An assembly for delivering an implant into a body vessel, the implant having a proximal coupling member, the assembly comprising: a sheath comprising a lumen, an inner surface, and a distal end; and an engagement member extending within the sheath lumen, the engagement member comprising a distal end portion having a socket extending from an outer surface of the distal end portion into the engagement member, the socket having an inner profile greater than an outer profile of the implant proximal coupling member to permit the implant proximal coupling member to be removably positionable within the socket, wherein in an engaged position, the socket is positioned proximal to the sheath distal end to permit the sheath inner surface and the socket to collectively restrict longitudinal movement of the implant proximal coupling member out of the socket, and wherein in a released position, the socket is positioned distal to the sheath distal end to permit the implant proximal coupling member to exit the socket.

Clause 15. The assembly of Clause 14, wherein the engagement member comprises a slotted hypotube and a distal band, the hypotube having inner and outer diameters, the band having an inner diameter equal to or greater than the hypotube outer diameter and an outer profile of the engagement member distal end portion to permit the engagement member distal end portion to be slidably receivable within the band.

Clause 16. The assembly of any of Clauses 14 or 15, wherein the hypotube outer diameter is less than 0.025".

Clause 17. The assembly of Clause 16, wherein the hypotube outer diameter is about 0.018".

Clause 18. The assembly of any of Clauses 14-17, wherein the socket of the engagement member distal end portion comprises a first void extending into the distal end portion at a first depth and a second void extending into the distal end portion at a second depth, less than the first depth, the second void extending from a distal end of the distal end portion proximally toward the first void.

Clause 19. The assembly of any of Clauses 14-18, wherein the engagement member comprises a core member coupled to the distal end portion, the core member having an outer diameter less than an outer diameter of the distal end portion.

Clause 20. The assembly of Clause 19, wherein the core member outer diameter is less than 0.020".

Clause 21. The assembly of any of Clauses 19-20, wherein the core member outer diameter is about 0.014".

Clause 22. The assembly of any of Clauses 14-21, further comprising a catheter having a lumen, the sheath extending within the catheter lumen.

Clause 23. The assembly of Clause 22, wherein the catheter has an outer diameter of about 0.036".

Clause 24. The assembly of any of Clauses 22 or 23, wherein the catheter comprises a marker band at a distal end thereof.

Clause 25. The assembly of Clause 24, wherein the marker band has an outer diameter of about 0.040".

Clause 26. The assembly of any of Clauses 14-25, further comprising a handle assembly, the handle assembly comprising (i) a first slidable member coupled to a proximal end of the engagement member and (ii) a second slidable member coupled to a proximal end of the sheath, the first and second slidable members having a first configuration in which the first and second slidable members are coupled together to move as a unit and a second configuration in which the first and second slidable members are movable relative to each other to cause the engagement member to move relative to the sheath.

Clause 27. The assembly of Clause 26, wherein the handle assembly comprises a spacer pin, the space or pin being removably engageable with the proximal end of the engagement member to secure a longitudinal position of the engagement member relative to the sheath.

Clause 28. The assembly of Clause 27, wherein the first slidable member comprises a first knob and the second slidable member comprises a second knob, the spacer pin being positionable between and in contact with the first and second knobs in the first configuration.

Clause 29. The assembly of any of Clauses 14-29, further comprising an ejection wire coupled to the engagement member distal end portion and extending proximally across the socket, the ejection wire having (i) a recessed configuration in which the ejection wire is slack and extends along a bottom surface of the socket and (ii) an ejection configuration in which the ejection wire is taut and extends transversely across the socket, wherein the ejection wire permits positioning of the implant proximal coupling member within the socket in the recessed configuration and movement of the ejection wire to the ejection configuration urges the implant proximal coupling member out of the socket.

Clause 30. The assembly of Clause 29, wherein the ejection wire extends proximally to a handle assembly, the handle assembly comprising an ejection actuator to permit proximal withdrawal of the ejection wire to cause the ejection wire to move to the ejection configuration.

Clause 31. An assembly for delivering an implant into a body vessel, the implant having a proximal coupling member, the assembly comprising: a sheath comprising a lumen, an inner surface, and a distal end; a core member extending within the sheath lumen, the core member comprising a lumen extending therethrough and a slot extending proximally from a distal end of the core member along an outer surface thereof; and a release wire extending within the core member lumen, the release wire having a distal portion extending out of the core member lumen beyond the core member distal end, wherein (i) in an engaged position, the core member distal end is positioned within the sheath lumen and the release wire distal portion reverses to loop into the core member slot to be interposed between the core member and the sheath inner surface and (ii) in a released position, the core member distal end is positioned distally beyond the sheath distal end and the release wire distal portion is positioned outside of the core member slot, wherein in the engaged position, the release wire distal portion loops around the implant proximal coupling member to constrain longitudinal movement of the implant proximal coupling member relative to the core member.

Clause 32. The assembly of Clause 31, wherein the release wire distal portion contacts the slot and the sheath inner surface in the engaged position.

Clause 33. The assembly of any of Clauses 31 or 32, wherein the release wire distal portion is resiliently biased away from the core member slot.

Clause 34. The assembly of any of Clauses 31-33, wherein the release wire distal portion is resiliently biased to a substantially straight configuration.

Clause 35. The assembly of any of Clauses 31-34, wherein the release wire distal portion comprises a length of at least about twice as long as a length of the implant proximal coupling member.

Clause 36. The assembly of Clause 35, wherein the release wire distal portion comprises a length of at least about 2.5 times as long as a length of the implant proximal coupling member.

Clause 37. The assembly of any of Clauses 31-36, wherein in the engaged position, the release wire distal portion extends into a loop of the implant.

Clause 38. An assembly for delivering an implant into a body vessel, the implant having a proximal coupling member, the assembly comprising: a sheath comprising a lumen, an inner surface, a distal end, and a longitudinal axis; and a core member extending longitudinally within the sheath lumen, the core member comprising a pusher member and at least one engagement arm extending distally of the pusher member, the engagement arm comprising a protrusion extending radially inwardly toward the longitudinal axis when the core member is positioned within the sheath lumen, the engagement arm having an engaged position in which the protrusion is spaced at a first distance from the longitudinal axis and a disengaged position in which the protrusion is spaced at a second distance from the longitudinal axis, the second distance being greater than the first distance.

Clause 39. The assembly of Clause 38, wherein the engagement arm is biased to radially diverge from the longitudinal axis.

Clause 40. The assembly of any one of Clauses 38 or 39, wherein the core member comprises a plurality of engagement arms.

Clause 41. The assembly of Clause 40, wherein each of the plurality of engagement arms is biased to radially diverge from each other when unconstrained by the sheath.

Clause 42. The assembly of any one of Clauses 40-41, wherein the pusher member is distally advanceable within the sheath lumen to move the plurality of engagement arms from the engaged position to the disengaged position.

Clause 43. The assembly of any one of Clauses 38-42, wherein the pusher member and the engagement arm are movable relative to each other.

Clause 44. The assembly of any one of Clauses 38-43, wherein the pusher member and the engagement arm are formed from separate components.

Clause 45. The assembly of any one of Clauses 38-44, wherein the protrusion is positioned at a distal end of the engagement arm.

Clause 46. The assembly of any one of Clauses 38-45, wherein the protrusion is positioned proximal to a distal end of the engagement arm.

Clause 47. The assembly of any one of Clauses 38-46, wherein in the engaged position, a distal end of the pusher member is longitudinally spaced apart from the protrusion to provide an engagement region in which the proximal coupling member of the implant is engaged.

Clause 48. An assembly for delivering an implant into a body vessel, the assembly comprising: a first slidable member comprising proximal and distal ends, the first slidable member being operably coupled to a pusher component, the first slidable member comprising an outer surface and a groove along the outer surface; a second slidable member comprising proximal and distal ends and a tubular component having a lumen through which the pusher component is disposed, the second slidable member being operably coupled to a sheath; and a release pin comprising a tab and an engagement portion, the engagement portion being removably couplable to the groove of the first slidable member to maintain a spacing between distal ends of the first slidable member and the second slidable member, the release pin being movable to permit the distal end of the first slidable member to be advanced distally toward the distal end of the second slidable member to facilitate release of the implant from the assembly.

Clause 49. The assembly of Clause 48, wherein the release pin comprises an open socket configured to engage with the groove of the first slidable member.

Clause 50. The assembly of any one of Clauses 48 or 49, wherein the release pin comprises an open socket configured to snap onto the groove of the first slidable member.

Clause 51. The assembly of any one of Clauses 48-50, wherein the groove comprises a circumferential indentation formed along the outer surface of the first slidable member.

Clause 52. The assembly of any one of Clauses 48-51, further comprising a main handle, the main handle comprising a tubular component having a lumen and a notch formed therein, the notch extending radially toward the lumen of the tubular component, the tubular component lumen being configured to receive the first and second slidable members therethrough, the second slidable member comprising a second groove, wherein the assembly further comprises a second release pin configured to extend through the main handle notch to engage the second groove of the second slidable member in a first configuration in which the first and second slidable members are longitudinally fixed relative to the main handle.

Clause 53. The assembly of Clause 52, wherein the second release pin comprises an open socket configured to engage with the second groove of the second slidable member.

Clause 54. The assembly of any one of Clauses 52 or 53, wherein the second release pin comprises an open socket configured to snap onto the second groove of the second slidable member.

Clause 54. An assembly comprising any of the devices, implants, or components recited in any one of Clauses 1-53.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method clauses present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the Clauses, such term is intended to be inclusive in a manner similar to the term "comprise" as "comprise" is interpreted when employed as a transitional word in a Clause.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof.

What is claimed is:

1. An assembly for delivering an implant into a body vessel, the implant having a proximal coupling member, the assembly comprising:
   a sheath comprising a lumen, an inner surface, and a distal end; and
   an engagement member extending within the sheath lumen, the engagement member comprising a distal end portion with a socket, the socket comprising a proximal connection cavity and an engagement cavity distal to the proximal connection cavity, the proximal connection cavity extending distally into the socket from a proximal surface of the socket, the engagement cavity extending partially into the socket from an outer surface of the socket to provide a void whereinto the implant proximal coupling member can be placed, the engagement cavity having an inner profile greater than an outer profile of the implant proximal coupling member to permit the implant proximal coupling member to be removably positionable within the engagement cavity, the inner profile comprising a spherical cavity, the outer profile of the implant proximal coupling member corresponding to the spherical cavity,
   wherein in an engaged position, the spherical cavity of the socket is positioned proximal to the sheath distal end to permit the sheath inner surface and the spherical cavity of the socket to collectively restrict longitudinal movement of the implant proximal coupling member out of the socket, and wherein in a released position, the socket is positioned distal to the sheath distal end to permit the implant proximal coupling member to exit the socket.

2. The assembly of claim 1, wherein the socket of the engagement member distal end portion comprises a first void extending into the distal end portion at a first depth and a second void extending into the distal end portion at a second depth, less than the first depth, the second void extending from a proximal end of the distal end portion distally toward the first void.

3. The assembly of claim 1, wherein the engagement member comprises a core member coupled to the distal end portion, the core member having an outer diameter less than an outer diameter of the distal end portion.

4. The assembly of claim 1, further comprising a catheter having a lumen, the sheath extending within the catheter lumen.

5. The assembly of claim 1, further comprising an ejection wire coupled to the engagement member distal end portion and extending proximally across the socket, the ejection wire having (i) a recessed configuration in which the ejection wire is slack and extends along a bottom surface of the socket and (ii) an ejection configuration in which the ejection wire is taut and extends transversely across the socket, wherein the ejection wire permits positioning of the implant proximal coupling member within the socket in the recessed configuration and movement of the ejection wire to the ejection configuration urges the implant proximal coupling member out of the socket.

6. The assembly of claim 5, wherein the ejection wire extends proximally to a handle assembly, the handle assembly comprising an ejection actuator to permit proximal withdrawal of the ejection wire to cause the ejection wire to move to the ejection configuration.

7. The assembly of claim 1, wherein the engagement cavity of the socket is configured such that when the implant proximal coupling member is placed thereinto, the implant proximal coupling member is exposed to the sheath inner surface along only a single circumferential segment of the socket.

8. The assembly of claim 1, wherein the engagement cavity comprises a longitudinally transverse cylindrical portion and a longitudinally extending cylinder segment portion.

9. The assembly of claim 8, wherein a longitudinal extent of the cylindrical portion is approximately equal to a longitudinal extent of the cylinder segment portion.

10. The assembly of claim 1, wherein the sheath comprises a hypotube and a distal band configured to receive a distal end of the hypotube having the engagement member at least partially disposed therein, the hypotube having inner and outer diameters, the band having an inner diameter equal to or greater than the hypotube outer diameter and an outer profile of the engagement member distal end portion to permit the engagement member distal end portion to be slidably receivable within the band.

11. The assembly of claim 1, wherein the assembly comprises the implant.

12. The assembly of claim 1, wherein the implant proximal coupling member comprises a spherical shape.

13. An assembly for delivering an implant into a body vessel, the implant having a proximal coupling member, the assembly comprising:
   a sheath comprising a lumen, an inner surface, and a distal end; and
   an engagement member extending within the sheath lumen, the engagement member comprising a distal end portion with a socket, the socket comprising a proximal connection cavity and a spherical engagement cavity distal to the proximal connection cavity, the proximal connection cavity extending distally into the socket from a proximal surface of the socket, the spherical engagement cavity extending partially into the socket from an outer surface of the socket whereinto the implant proximal coupling member can be placed, an outer profile of the implant proximal coupling member being mateable with an inner profile of the spherical engagement cavity,
   wherein in an engaged position, the spherical engagement cavity of the socket is positioned proximal to the sheath distal end to permit the sheath inner surface and the spherical engagement cavity of the socket to collectively restrict longitudinal movement of the implant proximal coupling member out of the socket, and wherein in a released position, the socket is positioned distal to the sheath distal end to permit the implant proximal coupling member to exit the socket.

14. The assembly of claim 13, wherein the assembly comprises the implant.

15. The assembly of claim 13, wherein the implant proximal coupling member comprises a spherical shape.

16. The assembly of claim 13, wherein the socket of the engagement member distal end portion comprises a first void extending into the distal end portion at a first depth and a second void extending into the distal end portion at a second depth, less than the first depth, the second void extending from a proximal end of the distal end portion distally toward the first void.

17. The assembly of claim 13, wherein the engagement member comprises a core member coupled to the distal end portion, the core member having an outer diameter less than an outer diameter of the distal end portion.

18. The assembly of claim 13, further comprising a catheter having a lumen, the sheath extending within the catheter lumen.

19. The assembly of claim 13, further comprising an ejection wire coupled to the engagement member distal end portion and extending proximally across the socket, the ejection wire having (i) a recessed configuration in which the ejection wire is slack and extends along a bottom surface of the socket and (ii) an ejection configuration in which the ejection wire is taut and extends transversely across the socket, wherein the ejection wire permits positioning of the implant proximal coupling member within the socket in the recessed configuration and movement of the ejection wire to the ejection configuration urges the implant proximal coupling member out of the socket.

* * * * *